(12) United States Patent
Gower et al.

(10) Patent No.: US 9,730,885 B2
(45) Date of Patent: Aug. 15, 2017

(54) EXTENDED RELEASE, ABUSE DETERRENT PHARMACEUTICAL COMPOSITIONS

(71) Applicant: Mallinckrodt LLC, Hazelwood, MO (US)

(72) Inventors: Brad L. Gower, O'Fallon, IL (US); Carlos H. Castaneda, St. Louis, MO (US); Jae Han Park, Olivette, MO (US); Clifford J. Herman, St. Louis, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 389 days.

(21) Appl. No.: 13/939,357

(22) Filed: Jul. 11, 2013

(65) Prior Publication Data

US 2014/0017310 A1 Jan. 16, 2014

Related U.S. Application Data

(60) Provisional application No. 61/670,751, filed on Jul. 12, 2012, provisional application No. 61/790,463, filed on Mar. 15, 2013.

(51) Int. Cl.
| | |
|---|---|
| *A61K 9/00* | (2006.01) |
| *A61K 9/20* | (2006.01) |
| *A61K 9/28* | (2006.01) |
| *A61K 31/485* | (2006.01) |

(52) U.S. Cl.
CPC .......... *A61K 9/0002* (2013.01); *A61K 9/2013* (2013.01); *A61K 9/2018* (2013.01); *A61K 9/2027* (2013.01); *A61K 9/2031* (2013.01); *A61K 9/2054* (2013.01); *A61K 9/28* (2013.01); *A61K 31/485* (2013.01)

(58) Field of Classification Search
CPC .. A61K 9/0002; A61K 9/2013; A61K 9/2018; A61K 9/2027; A61K 9/2031; A61K 9/2054; A61K 9/28; A61K 31/485
See application file for complete search history.

(56) References Cited

U.S. PATENT DOCUMENTS

| | | | |
|---|---|---|---|
| 4,070,494 A | 1/1978 | Hoffmeister et al. | |
| 4,753,801 A | 6/1988 | Oren et al. | |
| 5,266,331 A | 11/1993 | Oshlack et al. | |
| 5,460,826 A | 10/1995 | Merrill et al. | |
| 5,472,712 A | 12/1995 | Oshlack et al. | |
| 5,508,042 A | 4/1996 | Oshlack et al. | |
| 5,549,912 A | 8/1996 | Oshlack et al. | |
| 5,578,709 A | 11/1996 | Woiszwillo | |
| 5,656,295 A | 8/1997 | Oshlack et al. | |
| 5,700,478 A | 12/1997 | Biegajski et al. | |
| 5,709,883 A | 1/1998 | Drizen et al. | |
| 5,843,347 A | 12/1998 | Nguyen et al. | |
| 5,885,616 A | 3/1999 | Hsiao et al. | |
| 5,958,458 A | 9/1999 | Norling et al. | |
| 5,968,551 A | 10/1999 | Oshlack et al. | |
| 6,066,339 A | 5/2000 | Stark et al. | |
| 6,072,100 A | 6/2000 | Mooney et al. | |
| 6,090,925 A | 7/2000 | Woiszwillo et al. | |
| 6,103,261 A | 8/2000 | Chasin et al. | |
| 6,106,862 A | 8/2000 | Chen et al. | |
| 6,143,322 A | 11/2000 | Sackler et al. | |
| 6,143,353 A | 11/2000 | Oshlack et al. | |
| 6,177,102 B1 | 1/2001 | Chen et al. | |
| 6,245,357 B1 | 6/2001 | Edgren et al. | |
| 6,251,430 B1 | 6/2001 | Zhang et al. | |
| 6,268,053 B1 | 7/2001 | Woiszwillo et al. | |
| 6,309,668 B1 | 10/2001 | Bastin et al. | |
| 6,316,031 B1 | 11/2001 | Oshlack et al. | |
| 6,335,033 B2 | 1/2002 | Oshlack et al. | |
| 6,340,471 B1 | 1/2002 | Kershman et al. | |
| 6,342,250 B1 | 1/2002 | Masters | |
| 6,372,254 B1 | 4/2002 | Ting et al. | |
| 6,387,404 B2 | 5/2002 | Oshlack et al. | |
| 6,436,438 B1 | 8/2002 | Momberger et al. | |
| 6,458,387 B1 | 10/2002 | Scott et al. | |
| 6,488,963 B1 | 12/2002 | McGinity et al. | |
| 6,500,459 B1 | 12/2002 | Chhabra et al. | |
| 6,541,025 B1 | 4/2003 | Kershman et al. | |
| 6,572,885 B2 | 6/2003 | Oshlack et al. | |
| 6,673,369 B2 | 1/2004 | Rampal et al. | |
| 6,685,964 B1 | 2/2004 | Bartholomaeus et al. | |
| 6,706,281 B2 | 3/2004 | Oshlack et al. | |
| 6,730,321 B2 | 5/2004 | Ting et al. | |
| 6,733,783 B2 | 5/2004 | Oshlack et al. | |
| 6,893,661 B1 | 5/2005 | Odidi et al. | |
| 6,902,742 B2 | 6/2005 | Devane et al. | |
| 6,905,709 B2 | 6/2005 | Oshlack et al. | |

(Continued)

FOREIGN PATENT DOCUMENTS

| | | |
|---|---|---|
| EP | 2 123 274 A1 | 11/2009 |
| JP | 8-291051 | 5/1996 |

(Continued)

OTHER PUBLICATIONS

Beer et al., "Impact of slow-release oral morphine on drug abusing habits in Austria", Neuropsychiatrie, Dustri Verlag, Deisenhofen, DE, vol. 24, No. 2; Jan. 1, 2010; pp. 108-117.

(Continued)

*Primary Examiner* — Michael B Pallay

(57) ABSTRACT

Pharmaceutical compositions comprising at least one active pharmaceutical ingredient or a pharmaceutically acceptable salt thereof, at least one hydrophilic plastomer, at least one hydrophilic elastomer, and at least one deliquescent plasticizer, wherein the pharmaceutical compositions provide extended release of the API and have abuse deterrent properties. Methods for preparing the pharmaceutical compositions in which the components of the composition are humidified such that the deliquescent plasticizer deliquesces, thereby plasticizing the hydrophilic polymers.

13 Claims, 3 Drawing Sheets

(56) References Cited

U.S. PATENT DOCUMENTS

| | | |
|---|---|---|
| 6,916,485 B2 | 7/2005 | Aiache et al. |
| 6,923,988 B2 | 8/2005 | Patel et al. |
| 6,939,538 B2 | 9/2005 | Prescott et al. |
| 6,960,357 B2 | 11/2005 | Chopra |
| 6,962,717 B1 | 11/2005 | Huber et al. |
| 6,974,591 B2 | 12/2005 | Kendrup et al. |
| 7,070,806 B2 | 7/2006 | Oshlack et al. |
| 7,129,248 B2 | 10/2006 | Chapman et al. |
| 7,201,920 B2 | 4/2007 | Kumar et al. |
| 7,316,821 B2 | 1/2008 | Oshlack et al. |
| 7,338,668 B2 | 3/2008 | Lynenskhold et al. |
| 7,476,402 B2 | 1/2009 | Kumar et al. |
| 7,510,726 B2 | 3/2009 | Kumar et al. |
| 7,510,727 B2 | 3/2009 | Oshlack et al. |
| 7,514,100 B2 | 4/2009 | Oshlack et al. |
| 7,572,463 B2 | 8/2009 | Bartholomaeus et al. |
| 7,674,798 B2 | 3/2010 | Chapman et al. |
| 7,674,799 B2 | 3/2010 | Chapman et al. |
| 7,674,800 B2 | 3/2010 | Chapman et al. |
| 7,682,633 B2 | 3/2010 | Matthews et al. |
| 7,683,072 B2 | 3/2010 | Chapman et al. |
| 7,691,873 B2 | 4/2010 | Duncalf et al. |
| 7,776,314 B2 | 8/2010 | Bartholomaus et al. |
| 7,815,934 B2 | 10/2010 | Boehm |
| 7,842,307 B2 | 11/2010 | Oshlack et al. |
| 7,842,309 B2 | 11/2010 | Oshlack et al. |
| 7,842,311 B2 | 11/2010 | Oshlack et al. |
| 7,851,482 B2 | 12/2010 | Dung et al. |
| 7,879,362 B2 | 2/2011 | Castan et al. |
| 7,906,143 B1 | 3/2011 | Odidi et al. |
| 7,981,439 B2 | 7/2011 | Kumar et al. |
| 8,017,150 B2 | 9/2011 | Yang et al. |
| 8,075,872 B2 | 12/2011 | Arkenau-Maric et al. |
| 8,101,630 B2 | 1/2012 | Kumar et al. |
| 8,110,226 B2 | 2/2012 | Li |
| 8,114,383 B2 | 2/2012 | Bartholomaus et al. |
| 8,114,384 B2 | 2/2012 | Arkenau et al. |
| 8,142,811 B2 | 3/2012 | Oshlack et al. |
| 8,173,152 B2 | 5/2012 | Crowley et al. |
| 8,192,722 B2 | 6/2012 | Arkenau-Maric et al. |
| 8,202,542 B1 | 6/2012 | Mehta et al. |
| 8,236,351 B2 | 8/2012 | Oshlack et al. |
| 8,298,577 B2 | 10/2012 | Moe |
| 8,309,060 B2 | 11/2012 | Bartholomaus et al. |
| 8,309,122 B2 | 11/2012 | Kao et al. |
| 8,323,889 B2 | 12/2012 | Arkenau-Maric et al. |
| 8,329,216 B2 | 12/2012 | Kao et al. |
| 8,337,888 B2 | 12/2012 | Wright et al. |
| 8,357,399 B2 | 1/2013 | Oshlack et al. |
| 8,361,499 B2 | 1/2013 | Oshlack et al. |
| 8,372,432 B2 | 2/2013 | Han et al. |
| 8,377,453 B2 | 2/2013 | Han et al. |
| 8,377,994 B2 | 2/2013 | Gray et al. |
| 8,383,152 B2 | 2/2013 | Jans et al. |
| 8,389,007 B2 | 3/2013 | Wright et al. |
| 8,394,408 B2 | 3/2013 | Han et al. |
| 8,399,414 B2 | 3/2013 | Harada et al. |
| 8,415,401 B2 | 4/2013 | Yum et al. |
| 8,445,023 B2 | 5/2013 | Guimberteau et al. |
| 8,465,776 B2 | 6/2013 | Hoarau |
| 8,486,448 B2 | 7/2013 | Rahmouni et al. |
| 8,486,449 B2 | 7/2013 | Rahmouni et al. |
| 8,501,160 B2 | 8/2013 | Cailly-Dufestel et al. |
| 2001/0008639 A1 | 7/2001 | Oshlack et al. |
| 2002/0058050 A1 | 5/2002 | Sackler et al. |
| 2002/0192287 A1 | 12/2002 | Mooney et al. |
| 2003/0091635 A1 | 5/2003 | Baichwal et al. |
| 2003/0118641 A1 | 6/2003 | Maloney et al. |
| 2003/0129234 A1 | 7/2003 | Baichwal et al. |
| 2003/0157167 A1 | 8/2003 | Kao et al. |
| 2003/0211157 A1 | 11/2003 | Simon |
| 2004/0052843 A1 | 3/2004 | Lerner et al. |
| 2004/0062812 A1 | 4/2004 | Maloney |
| 2004/0131552 A1 | 7/2004 | Boehm |
| 2004/0241234 A1 | 12/2004 | Vilkov |
| 2005/0142203 A1 | 6/2005 | Heinicke |
| 2005/0163856 A1 | 7/2005 | Maloney et al. |
| 2005/0186139 A1 | 8/2005 | Bartholomaus et al. |
| 2005/0191244 A1 | 9/2005 | Bartholomaus et al. |
| 2005/0196459 A1 | 9/2005 | Castan et al. |
| 2005/0214223 A1 | 9/2005 | Bartholomaeus et al. |
| 2005/0226929 A1 | 10/2005 | Xie et al. |
| 2005/0236741 A1 | 10/2005 | Arkenau et al. |
| 2005/0245557 A1 | 11/2005 | Schoenhard |
| 2005/0266078 A1 | 12/2005 | Jorda et al. |
| 2006/0002860 A1 | 1/2006 | Bartholomaus et al. |
| 2006/0110327 A1 | 5/2006 | Emigh et al. |
| 2006/0153918 A1 | 7/2006 | Lerner et al. |
| 2006/0165791 A1 | 7/2006 | Oshlack et al. |
| 2006/0193782 A1 | 8/2006 | Bartholomaus et al. |
| 2006/0233879 A1 | 10/2006 | Lerner et al. |
| 2006/0233880 A1 | 10/2006 | Lerner et al. |
| 2006/0263429 A1 | 11/2006 | Feng |
| 2006/0275367 A1 | 12/2006 | Chungi |
| 2007/0003616 A1 | 1/2007 | Arkenau-Maric et al. |
| 2007/0048228 A1 | 3/2007 | Arkenau-Maric et al. |
| 2007/0098792 A1 | 5/2007 | Kao et al. |
| 2007/0098793 A1 | 5/2007 | Kao et al. |
| 2007/0140975 A1 | 6/2007 | Baichwal et al. |
| 2007/0183980 A1 | 8/2007 | Arkenau-Maric et al. |
| 2007/0190142 A1 | 8/2007 | Breitenbach et al. |
| 2007/0212414 A1 | 9/2007 | Baichwal et al. |
| 2007/0224129 A1 | 9/2007 | Guimberteau et al. |
| 2007/0231268 A1 | 10/2007 | Emigh et al. |
| 2007/0243245 A1 | 10/2007 | Heinicke |
| 2007/0275065 A1 | 11/2007 | Oshlack et al. |
| 2007/0281016 A1 | 12/2007 | Kao et al. |
| 2007/0281017 A1 | 12/2007 | Kao et al. |
| 2007/0298103 A1 | 12/2007 | Hayes |
| 2008/0008659 A1 | 1/2008 | Guimberteau et al. |
| 2008/0014257 A1 | 1/2008 | He et al. |
| 2008/0020039 A1 | 1/2008 | Parikh et al. |
| 2008/0031949 A1 | 2/2008 | Hamed et al. |
| 2008/0057129 A1 | 3/2008 | Lerner et al. |
| 2008/0069871 A1* | 3/2008 | Vaughn ............... A61K 9/2013 424/456 |
| 2008/0075770 A1 | 3/2008 | Vaughn et al. |
| 2008/0085304 A1 | 4/2008 | Baichwal et al. |
| 2008/0102121 A1 | 5/2008 | Devane et al. |
| 2008/0152595 A1 | 6/2008 | Emigh et al. |
| 2008/0187579 A1 | 8/2008 | Bhat et al. |
| 2008/0193540 A1 | 8/2008 | Soula et al. |
| 2008/0247959 A1 | 10/2008 | Bartholomaus et al. |
| 2008/0248113 A1 | 10/2008 | Bartholomaus et al. |
| 2008/0260844 A1 | 10/2008 | Soula et al. |
| 2008/0311187 A1 | 12/2008 | Ashworth et al. |
| 2008/0311197 A1 | 12/2008 | Arkenau-Maric et al. |
| 2008/0317854 A1 | 12/2008 | Arkenau et al. |
| 2009/0005408 A1 | 1/2009 | Arkenau-Maric et al. |
| 2009/0053310 A1 | 2/2009 | Pilgaonkar et al. |
| 2009/0068269 A1 | 3/2009 | Oshlack et al. |
| 2009/0081290 A1 | 3/2009 | McKenna et al. |
| 2009/0098200 A1 | 4/2009 | Temtsin Krayz et al. |
| 2009/0124650 A1 | 5/2009 | Ahdieh |
| 2009/0175937 A1 | 7/2009 | Rahmouni et al. |
| 2009/0192183 A1 | 7/2009 | Kao et al. |
| 2009/0238873 A1 | 9/2009 | Chattaraj et al. |
| 2009/0317355 A1 | 12/2009 | Roth et al. |
| 2010/0015223 A1 | 1/2010 | Cailly-Dufestel et al. |
| 2010/0080829 A1 | 4/2010 | Dulieu et al. |
| 2010/0092570 A1 | 4/2010 | Oshlack et al. |
| 2010/0099696 A1 | 4/2010 | Soscia et al. |
| 2010/0120723 A1 | 5/2010 | Akbarieh et al. |
| 2010/0151028 A1 | 6/2010 | Ashworth et al. |
| 2010/0168148 A1 | 7/2010 | Wright et al. |
| 2010/0209495 A1 | 8/2010 | Li et al. |
| 2010/0221322 A1 | 9/2010 | Bartholomaus et al. |
| 2010/0260833 A1 | 10/2010 | Bartholomaus et al. |
| 2011/0002985 A1 | 1/2011 | Shah et al. |
| 2011/0020444 A1 | 1/2011 | Kao et al. |
| 2011/0020451 A1* | 1/2011 | Bartholomaus ...... A61K 9/2013 424/486 |
| 2011/0033537 A1 | 2/2011 | Gervais et al. |
| 2011/0038930 A1 | 2/2011 | Barnscheid et al. |

(56) References Cited

U.S. PATENT DOCUMENTS

| | | |
|---|---|---|
| 2011/0054038 A1 | 3/2011 | Glozman |
| 2011/0077238 A1 | 3/2011 | Leech et al. |
| 2011/0091488 A1 | 4/2011 | Halliday et al. |
| 2011/0091537 A1 | 4/2011 | Castan et al. |
| 2011/0123613 A1 | 5/2011 | Bhat et al. |
| 2011/0142943 A1 | 6/2011 | Rariy et al. |
| 2011/0150970 A1 | 6/2011 | Shah et al. |
| 2011/0150971 A1 | 6/2011 | Shah et al. |
| 2011/0150991 A1 | 6/2011 | Shah et al. |
| 2011/0159089 A1 | 6/2011 | Shah et al. |
| 2011/0159090 A1 | 6/2011 | Shah et al. |
| 2011/0200681 A1 | 8/2011 | Habib et al. |
| 2011/0230510 A1 | 9/2011 | Oshlack et al. |
| 2011/0301129 A1 | 12/2011 | Berner et al. |
| 2011/0311631 A1 | 12/2011 | Baer et al. |
| 2012/0034171 A1 | 2/2012 | Arkenau-Maric et al. |
| 2012/0059065 A1 | 3/2012 | Barnscheid et al. |
| 2012/0065220 A1* | 3/2012 | Barnscheid .......... A61K 31/137 514/282 |
| 2012/0083506 A1 | 4/2012 | Herry et al. |
| 2012/0101118 A1 | 4/2012 | Fleischer et al. |
| 2012/0128848 A1 | 5/2012 | Yang et al. |
| 2012/0135071 A1 | 5/2012 | Bartholomaus et al. |
| 2012/0135075 A1 | 5/2012 | Mohammad |
| 2012/0136021 A1 | 5/2012 | Barnscheid et al. |
| 2012/0141583 A1 | 6/2012 | Mannion et al. |
| 2012/0148672 A1 | 6/2012 | Mehta et al. |
| 2012/0156277 A1 | 6/2012 | Shah et al. |
| 2012/0164209 A1 | 6/2012 | Shah et al. |
| 2012/0164220 A1 | 6/2012 | Huang |
| 2012/0165361 A1 | 6/2012 | Cruz et al. |
| 2012/0202838 A1 | 8/2012 | Ghosh et al. |
| 2012/0207825 A1 | 8/2012 | Roy et al. |
| 2012/0214777 A1 | 8/2012 | Crowley et al. |
| 2012/0231075 A1 | 9/2012 | Kao et al. |
| 2012/0251637 A1 | 10/2012 | Bartholomaus et al. |
| 2012/0252832 A1 | 10/2012 | Caruso et al. |
| 2012/0252845 A1 | 10/2012 | Engqvist |
| 2012/0301546 A1 | 11/2012 | Hassan |
| 2012/0308654 A1 | 12/2012 | Bartholomaus et al. |
| 2012/0321674 A1 | 12/2012 | Vachon et al. |
| 2012/0321716 A1 | 12/2012 | Vachon et al. |
| 2012/0328707 A1 | 12/2012 | Hermann |
| 2013/0005977 A1 | 1/2013 | Chapman et al. |
| 2013/0011543 A1 | 1/2013 | Oshlack et al. |
| 2013/0012533 A1 | 1/2013 | Oshlack et al. |
| 2013/0022646 A1 | 1/2013 | Rudnic et al. |
| 2013/0028955 A1 | 1/2013 | Tolia |
| 2013/0028970 A1 | 1/2013 | Schwier et al. |
| 2013/0039932 A1 | 2/2013 | Park et al. |
| 2013/0059010 A1 | 3/2013 | Herry et al. |
| 2013/0129825 A1 | 5/2013 | Billoet |
| 2013/0171075 A1 | 7/2013 | Arkenau-Maric et al. |
| 2013/0171257 A1 | 7/2013 | Kumar et al. |
| 2013/0195935 A1 | 8/2013 | Bartholomaus et al. |
| 2013/0217716 A1 | 8/2013 | Wright et al. |
| 2013/0225625 A1 | 8/2013 | Barnscheid et al. |
| 2013/0225697 A1 | 8/2013 | Barnscheid et al. |
| 2013/0280176 A1 | 10/2013 | Diezi et al. |
| 2013/0280177 A1 | 10/2013 | Raman et al. |
| 2014/0017310 A1* | 1/2014 | Gower .................. A61K 9/0002 424/474 |

FOREIGN PATENT DOCUMENTS

| | | |
|---|---|---|
| WO | 2007009806 A2 | 1/2007 |
| WO | 2008-011595 A2 | 1/2008 |
| WO | 2008011595 A2 | 1/2008 |
| WO | 2008-086804 A2 | 7/2008 |
| WO | 2008086804 A2 | 7/2008 |
| WO | 2011/013082 A1 | 2/2011 |
| WO | 2011/068723 A1 | 6/2011 |
| WO | 2011/079074 A1 | 6/2011 |
| WO | 2011/090724 A2 | 7/2011 |
| WO | 2011/090725 A2 | 7/2011 |
| WO | 2011/106076 A1 | 9/2011 |
| WO | 2012/028317 A1 | 3/2012 |
| WO | 2012-028318 A1 | 3/2012 |
| WO | 2012/028318 A1 | 3/2012 |
| WO | 2012/028319 A1 | 3/2012 |
| WO | 2012/061779 A1 | 5/2012 |
| WO | 2012/076907 A2 | 6/2012 |
| WO | 2012/080833 A2 | 6/2012 |
| WO | 2012/085656 A2 | 6/2012 |
| WO | 2012/085657 A2 | 6/2012 |
| WO | 2012/112952 A1 | 8/2012 |
| WO | 2012/162492 A1 | 11/2012 |
| WO | 2013/000578 A1 | 1/2013 |
| WO | 2013/003845 A1 | 1/2013 |
| WO | 2013/017234 A1 | 2/2013 |
| WO | 2013/018050 A2 | 2/2013 |
| WO | 2013/022924 A1 | 2/2013 |
| WO | 2013/057570 A2 | 4/2013 |
| WO | 2013/158810 A1 | 10/2013 |
| WO | 2013/158814 A1 | 10/2013 |
| WO | 2014/011830 A1 | 1/2014 |

OTHER PUBLICATIONS

International Search Report and Written Opinion from related International Patent Application No. PCT/US2013/050005, dated Aug. 19, 2013; 12 pgs.

International Search Report and Written Opinion from related International Patent Application No. PCT/US2013/037056, dated Jun. 24, 2013; 9 pgs.

International Search Report and Written Opinion from related International Patent Application No. PCT/US2013/037046, dated Jul. 3, 2013; 12 pgs.

Office action dated Mar. 7, 2016 from related Japanese application No. 2015-521793, 14 pgs.

Office action dated Jul. 12, 2016 from related Japanese application No. 2015-521793, 5 pgs.

Office action dated Feb. 24, 2016 from related Canadian application No. 2,877,774, 4 pgs.

Examination Report dated Mar. 2, 2017 from related EP Application No. 13 739 584.4, 4 pgs.

* cited by examiner

EXTENDED RELEASE, ABUSE DETERRENT PHARMACEUTICAL COMPOSITIONS

CROSS REFERENCE TO RELATED APPLICATIONS

This application claims the benefit of U.S. Provisional Application No. 61/670,751 filed Jul. 12, 2012 and U.S. Provisional Application No. 61/790,463 filed Mar. 15, 2013 which is incorporated herein in its entirety and U.S.

FIELD OF THE INVENTION

The present disclosure generally relates to pharmaceutical compositions that provide extended release of active ingredients and have abuse deterrent properties.

BACKGROUND OF THE INVENTION

In 2008 it was reported that non-medical use of pain relievers among the population aged 12 or older in the United States was second highest in prevalence among illicit drugs, after marijuana. Abuse of prescription pharmaceutical products follows the increasing availability of opioid dosage forms due to the more aggressive treatment of chronic pain in the populace. The increasing number of abusers, increasing availability, and the destructive/addictive potential of opiates make prescription pharmaceutical abuse a matter of public health concern.

Several routes of administration are commonly attempted by abusers. For example, the pharmaceutical dosage form may be chewed, or it may be crushed or pulverized into a powder and administered intranasally (i.e., snorted). Alternatively, the intact or tampered pharmaceutical dosage form may be dissolved in a suitable solvent and administered parenterally (i.e., injected intravenously), or the intact or tampered dosage form may be smoked.

To deter misuse and/or abuse of pharmaceutical dosage forms with extended drug release, multiple strategies have been employed. First, a chemical approach has been utilized to include an opioid antagonist in opioid pharmaceutical dosage forms. The opioid antagonist, which is not orally active, will substantially block the analgesic effects of the opioid when one attempts to abuse the tampered dosage form via snorting or injecting. Second, aversive agents and/or bitter agents have been added to pharmaceutical formulations to prevent abuse of the active pharmaceutical ingredient. This approach, however, could cause adverse effects in the patient population due to the properties associated with these agents. Third, a safer alternative is to incorporate excipients that provide a physical barrier in which abuse of the API is deterred. In one case, this is accomplished by incorporating the API into a polymeric matrix tablet containing high molecular weight gel forming polymers such as polyethylene oxide. The polymeric matrix tablet has increased hardness and retains a plastic-like nature after curing at a temperature above the softening temperature of the polyethylene oxide. The resultant tablet dosage form is difficult to crush or chew and forms a viscous gel when the dosage form comes into contact with a suitable solvent. However, because polyethylene oxide forms oxidative peroxide radicals when heated, APIs susceptible to oxidative degradation should be incorporated into such dosage forms with care. Alternately, the conditions for curing the dosage form with an API sensitive to oxidation must be tightly controlled, sometimes limiting the tamper resistant properties thereof. Similarly, thermolabile APIs cannot be incorporated into these cured dosage forms.

To impart abuse deterrent properties to pharmaceutical dosage forms comprising polymers, the polymers generally need to be plasticized. Typically, polymers are plasticized by plasticizers using either of two commonly used methods that thoroughly incorporate the plasticizers into the polymers. The most common method is hot melt extrusion. In this process, polymers and plasticizers are intimately mixed under heat and pressure and then extruded out of small orifices. Recent strides in this technique have resulted in acceptable material throughput for large scale manufacturing. A less common method for incorporating a plasticizer into a polymer involves dissolving the polymer and the plasticizer in a suitable co-solvent and then spray drying the mixture. This method has a very low material throughput and also has the significant technical issue of the plasticized polymers sticking to the spray drier. However, in both of these methods, the resultant plasticized polymer mass can be a sticky, non-flowable material that poses additional processing problems in milling, blending, and compressing with conventional manufacturing equipment.

Thus, there is a need for pharmaceutical dosage forms comprised of polymers that provide extended release of the API and are resistant to abuse and/or misuse. Additionally, there is a need for the easy manufacture of a plasticized polymer mass into a dosage form utilizing conventional processing equipment.

SUMMARY OF THE INVENTION

The present disclosure provides a tamper resistant, extended release comprising at least one active pharmaceutical ingredient (API) or a pharmaceutically acceptable salt thereof, at least one hydrophilic plastomer, optionally at least one hydrophilic elastomer, and at least one deliquescent plasticizer. The pharmaceutical composition disclosed herein provides extended release of the API and has abuse deterrent properties.

A further aspect of the present disclosure provides a process for preparing a solid dosage form. The process comprises: (a) forming a mixture comprising at least one hydrophilic plastomer, optionally at least one hydrophilic elastomer, and at least one deliquescent plasticizer, wherein the mixture is a powder, a granulate, or a solid dosage unit; (b) humidifying the mixture of (a) to form a humidified powder, a humidified granulate, or a humidified solid dosage unit; (c) optionally forming the humidified powder or the humidified granulate into a treated solid dosage unit; (d) optionally coating the humidified solid dosage unit of (b) or the treated solid dosage unit of (c) to form a coated solid dosage unit; and (e) heating the humidified solid dosage unit of (b), the treated solid dosage unit of (c), or the coated solid dosage unit of (d) to form the solid dosage form.

Other aspects and iterations of the disclosure are described in more detail below.

DETAILED DESCRIPTION OF THE INVENTION

Figure 1:
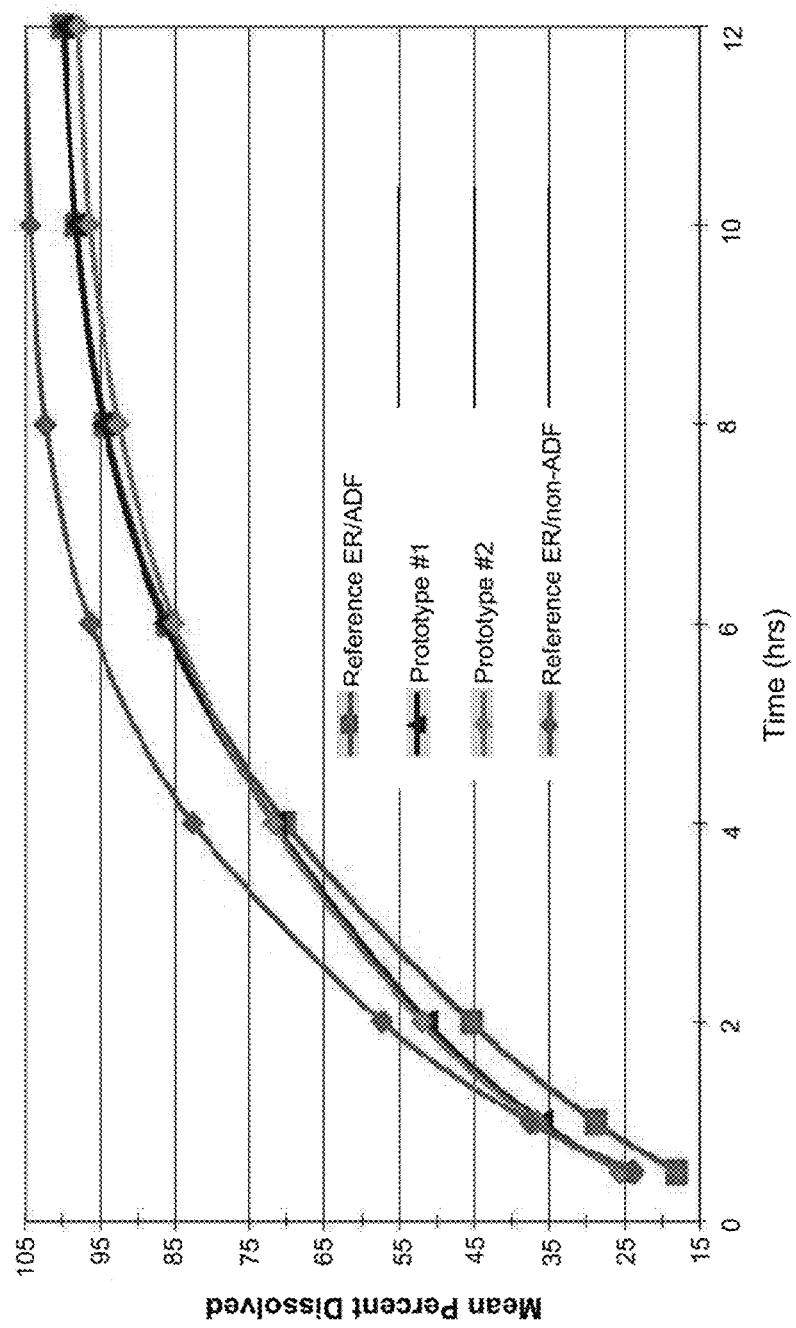
FIG. 1 shows extended release of the API. Plotted is the mean percent in vitro release of oxycodone HCl over a 12 hour period for prototype #1, prototype #2, a reference extended release (ER)/abuse deterrent formulation (ADF) oxycodone formulation, and a reference ER/non-ADF oxycodone formulation.

The present disclosure provides solid dosage pharmaceutical compositions that provide extended release of an active pharmaceutical ingredient and have abuse deterrent properties. Also provided are methods for making the extended release, abuse deterrent pharmaceutical compositions. The pharmaceutical compositions disclosed herein comprise at least one hydrophilic plastomer, optionally at least one hydrophilic elastomer, and at least one deliquescent plasticizer. Applicants of the present invention discovered that the hydrophilic polymers can be plasticized with deliquescent plasticizer by humidification of the composition comprising the polymers. Under a humid environment, the deliquescent plasticizer absorbs moisture from the atmosphere to become a liquid, thereby allowing the plasticizer to effectively plasticize the hydrophilic polymers. The humidified composition is then heated to remove excess moisture and to cure the hydrophilic polymers. The resultant composition has sufficient hardness and resiliency such that it resists being crushed or ground into fine particles.

(I) Pharmaceutical Composition

One aspect of the present disclosure provides extended release, abuse deterrent pharmaceutical compositions. Detailed below are the components of the composition, dosage forms of the composition, release characteristics of the composition, and abuse deterrent properties of the composition.

(a) Components of the Composition

The pharmaceutical composition disclosed herein comprises at least one hydrophilic plastomer, optionally at least one hydrophilic elastomer, and at least one deliquescent plasticizer. The combination of hydrophilic plastomers and optional hydrophilic elastomer, when suitably plasticized by the deliquescent plasticizer and heat-treated, creates a functional abuse deterrent composition.

(i) Hydrophilic Plastomer

The pharmaceutical composition comprises at least one hydrophilic plastomer. The term "hydrophilic" refers to a substance with affinity for water that readily absorbs and/or dissolves in water, and the term "plastomer" refers to a hard, rigid polymeric substance. More specifically, a hydrophilic plastomer refers to any polymeric substance that imparts hardness to a solid dosage form matrix when plasticized and/or cured.

The hydrophilic plastomer may be water soluble, water swellable, thermoplastic, or any combination thereof, and the hydrophilic plastomer may be natural, semi-synthetic, or synthetic. Non-limiting examples of suitable hydrophilic plastomers include cellulose ethers (such as, e.g., hydroxypropyl cellulose (HPC), methyl cellulose, hydroxymethyl cellulose, hydroxyethyl cellulose, hydroxypropylmethyl cellulose (HPMC), carboxymethyl cellulose, and the like); polyalkylene oxides (such as, e.g., polyethylene oxide (PEG), polypropylene oxide, and copolymers thereof); polyalkylene glycols (such as, e.g., polyethylene glycol, polypropylene glycol, and copolymers thereof); polyolefinic alcohols (such as, e.g., polyvinyl alcohol); polyvinyl lactams (such as, e.g., polyvinylpyrrolidone); polyvinyl alcohol/polyvinylpyrrolidone copolymers; polycarboxylic acids; polysaccharides (such as, e.g., celluloses, dextrans, gums derived from microbes or plants, starches, pectins, chitin, chitosan, and the like); polypeptides (such as, e.g., gelatin, albumin, polylysine, soy protein, and so forth); and combinations or copolymers of any of the foregoing. In exemplary embodiments, the hydrophilic plastomer may be hydroxypropyl cellulose, hydroxypropylmethyl cellulose, polyethylene oxide, or combinations thereof.

The hydrophilic plastomer may have a molecular weight ranging from about 20,000 daltons (Da) to about 2,000,000 Da. In various embodiments, the molecular weight of the hydrophilic plastomer may range from about 20,000 Da to about 100,000 Da, from about 100,000 Da to about 400,000 Da, from about 400,000 Da to about 1,000,000 Da, or from about 1,000,000 Da to about 2,000,000 Da. In one exemplary embodiment, the hydrophilic plastomer may have a molecular weight ranging from about 100,000 Da to about 200,000 Da. In another exemplary embodiment, the hydrophilic plastomer may have a molecular weight ranging from about 800,000 Da to about 900,000 Da.

The amount of hydrophilic plastomer present in the pharmaceutical composition can and will vary depending upon the identity of the hydrophilic plastomer, as well as the identity and/or amount of the other components utilized in the pharmaceutical composition. In general, the amount of hydrophilic plastomer present in the pharmaceutical composition may range from about 10% to about 90% by weight of the composition. In various embodiments, the amount of the hydrophilic plastomer present in the pharmaceutical composition may range from about 10% to about 20%, from about 20% to about 30%, from about 30% to about 40%, from about 40% to about 50%, or from about 50% to about 60%, from about 60% to about 70%, from about 70% to about 80%, or from about 80% to about 90% by weight of the pharmaceutical composition. In exemplary embodiments, the amount of the hydrophilic plastomer present may range from 30% to about 80% by weight of the pharmaceutical composition.

(ii) Hydrophilic Elastomer

The pharmaceutical composition disclosed herein may comprise at least one hydrophilic elastomer. The term "elastomer" refers to a substance with viscoelasticity, generally having a low Young's modulus (i.e., low rigidity) and a high strain yield (i.e., high deformability). The inclusion of a hydrophilic elastomer in the composition may counter the brittleness of the hydrophilic plastomer(s).

The hydrophilic elastomer may be water soluble and/or water swellable; and the elastomer may be natural, semi-synthetic, or synthetic. As will be appreciated by those skilled in the art, the molecular size of the elastomer can and will vary depending upon the identity of the elastomer. Suitable hydrophilic elastomers include, without limit, polyacrylates, polymethacrylates, combinations thereof, or copolymers thereof. Non-limiting examples of suitable polyacrylates include carbomers, which are homopolymers of acrylic acid crosslinked with a polyalcohol allyl ether (e.g., allyl ether pentaerythritol, allyl ether of sucrose, allyl ether of propylene), and polycarbophil, which is a homopolymer of acrylic acid crosslinked with divinyl glycol. Suitable hydrophilic methacrylate polymers include, but are not limited to, polyhydroxyethyl methacrylate, copolymers of methyl methacrylate and ethyl acrylate, and the like. In one embodiment, the hydrophilic elastomer may be a carbomer.

The amount of hydrophilic elastomer present in the pharmaceutical composition can and will vary depending upon the identity of the hydrophilic elastomer, as well as the identity and/or the amount of the hydrophilic plastomer(s) present in the pharmaceutical composition. In embodiments in which the hydrophilic elastomer is present, the amount of hydrophilic elastomer present in the pharmaceutical composition may range from about 0.5% to about 40% by weight of the composition. In various embodiments, the amount of hydrophilic elastomer present in the pharmaceutical composition may range from about 0.5% to about 2%, from about 2% to about 5%, from about 5% to about 10%, or from about 10% to about 20%, or from about 20% to about 40% by weight of the pharmaceutical composition. In exemplary embodiments, the pharmaceutical composition comprises the hydrophilic elastomer at an amount ranging from about 0.5% to about 10% by weight of the composition. In other embodiments, the hydrophilic elastomer is not present.

(iii) Deliquescent Plasticizer

The pharmaceutical composition disclosed herein also comprises at least one deliquescent plasticizer. In general, plasticizers increase the plasticity or fluidity of a material. A "deliquescent plasticizer" refers to a compound that is able to absorb moisture from the air such that it forms a saturated solution. Deliquescence occurs when the partial vapor pressure of the deliquescent plasticizer is less than the partial pressure of water vapor in the air. As a consequence, the deliquescent plasticizer liquefies and its mobility increases. Thus, in the pharmaceutical composition disclosed herein, humidification of a mixture comprising the hydrophilic plastomer, the hydrophilic elastomer, and the deliquescent plasticizer allows the deliquescent plasticizer to become liquid such that it can incorporate into the hydrophilic plastomer and the hydrophilic elastomer, thereby plasticizing the hydrophilic plastomer and the hydrophilic elastomer.

The deliquescent plasticizer may be an organic acid, a sugar alcohol, a co-processed mixture of an organic acid and/or a sugar alcohol and a liquid plasticizer, or combinations thereof. Non-limiting examples of suitable organic acids include citric acid, glutaric acid, malic acid, tartaric acid, and the like. In one embodiment, the organic acid may be citric acid. Suitable sugar alcohols include, without limit, sorbitol, xylitol, maltitol, and the like. In another embodiment, the sugar alcohol may be sorbitol. In general, the organic acid and the sugar alcohol are in solid forms. Non-limiting examples of suitable liquid plasticizers include glycerol (glycerin), polyethylene glycols (e.g., PEG 300, PEG 400, PEG 600, PEG 1000, etc.), triethyl citrate, tributyl citrate, acetyl triethyl citrate, triacetin (i.e., glycerol triacetal), dibutyl sebacate, diethyl phthalate, dibutyl phthalate, and combinations thereof. In one embodiment, the co-processed mixture may comprise sorbitol and PEG. In another embodiment, the co-processed mixture may comprise sorbitol and glycerol.

A co-processed mixture of an organic acid and/or a sugar alcohol and a liquid plasticizer may be prepared by contacting a solid form of the organic acid and/or the sugar alcohol with the liquid plasticizer. In general, the liquid plasticizer contacts the surface of the solid form of the organic acid and/or the sugar alcohol. The ratio of the liquid plasticizer to the organic acid and/or the sugar alcohol can and will vary. For example, the ratio of the liquid plasticizer to the organic acid and/or the sugar alcohol may be about 1:99, about 5:95, about 10:90, about 15:85, about 20:80, about 25:75, about 30:70, about 40:60, or any ratio there between. In some embodiments, the liquid plasticizer may be mixed with a suitable solvent. A suitable solvent is a solvent in which the liquid plasticizer dissolves, but the solid organic acid and/or sugar alcohol does not dissolve. Non-limiting examples of suitable solvents include alcohols, such as methanol, ethanol, isopropanol, propanol, and the like. In an embodiment in which the liquid plasticizer is glycerol, the solvent may be isopropanol. Contact between the liquid plasticizer and the solid form of the organic acid and/or the sugar alcohol may be performed in a fluid bed coater, a low shear planetary mixer, or any other suitable device known in the art.

In exemplary embodiments, the deliquescent plasticizer may be citric acid, a combination of citric acid and sorbitol, or a combination of citric acid and a co-processed mixture of sorbitol and glycerol.

In embodiments in which the deliquescent plasticizer comprises an organic acid, the amount of organic acid present in the pharmaceutical composition may range from about 1% to about 20% by weight of the pharmaceutical composition. In various iterations, the amount of organic acid present in the pharmaceutical composition may range from about 1% to about 5%, from about 5% to about 10%, from about 10% to about 15%, or from about 15% to about 20% by weight of the pharmaceutical composition.

In embodiments in which the deliquescent plasticizer comprises a sugar alcohol, the amount of sugar alcohol present in the pharmaceutical composition may range from about 1% to about 15% by weight of the pharmaceutical composition. In certain iterations, the amount of sugar alcohol present in the pharmaceutical composition may range from about 1% to about 5%, from about 5% to about 10%, or from about 10% to about 15% by weight of the pharmaceutical composition.

In embodiments in which the deliquescent plasticizer comprises a co-processed blend of a sugar alcohol and a liquid plasticizer, the amount of the co-processed blend present in the pharmaceutical composition may range from about 5% to about 25% by weight of the pharmaceutical composition. In some iterations, the amount of the co-processed blend present in the pharmaceutical composition may range from about 5% to about 10%, from about 10% to about 15%, from about 15% to about 20%, or from about 20% to about 25% by weight of the pharmaceutical composition.

The total amount of deliquescent plasticizer present in the pharmaceutical composition can and will vary depending upon the identities and/or amounts of the hydrophilic plastomers and elastomers present in the pharmaceutical composition. In general, the total amount of the deliquescent plasticizer present in the composition may range from about 2% to about 50% by weight of the pharmaceutical composition. In some embodiments, the total amount of the deliquescent plasticizer present may range from about 5% to about 40% by weight of the pharmaceutical composition. In other embodiments, the total amount of the deliquescent plasticizer present may range from about 10% to about 30% by weight of the pharmaceutical composition. In various embodiments, the total amount of the deliquescent plasticizer present in the pharmaceutical composition may range from about 5% to about 10%, from about 10% to about 15%, from about 15% to about 20%, from about 20% to about 25%, from about 25% to about 30%, from about 30% to about 40%, or from about 40% to about 50% by weight of the pharmaceutical composition. In exemplary embodiments, the total amount of the deliquescent plasticizer present may range from about 10% to about 30% by weight of the pharmaceutical composition.

(iv) Optional Modifying Agents

The pharmaceutical composition disclosed herein may optionally include one or more modifying agents that improve the abuse deterrent properties, add additional abuse deterrent features, and/or facilitate preparation (e.g., manufacturability) of the pharmaceutical composition. The modifying agent may be a hydrophilic gelling polymer, a clay mineral, a super-disintegrant, an alkalizing agent, a lubricant, or combinations thereof.

Hydrophilic gelling polymer. The optional modifying agent may be a hydrophilic gelling polymer. Hydrophilic gelling polymers, which are well known in the art, form viscous mixtures or gels when in contact with a suitable solvent. Inclusion of a gelling polymer may increase the gelling rate kinetics and/or overall gel viscosity when the pharmaceutical composition disclosed herein is in contact with a small volume of a suitable solvent. As a consequence, the resultant viscous mixture is difficult to draw into a syringe, thereby making it difficult or impossible to inject. Thus, the presence of the hydrophilic gelling polymer may provide another tampering deterrent feature to the pharmaceutical composition. Non-limiting examples of hydrophilic polymers are presented above in sections (I)(a)(i)-(ii). In one embodiment, the hydrophilic gelling polymer may be a cellulose ether. For example, the hydrophilic gelling polymer may be hydroxypropylmethyl cellulose (HPMC). In exemplary embodiments, the hydrophilic gelling polymer may be hydroxypropylmethyl cellulose having a molecular weight of about 150,000 Da.

In embodiments in which the hydrophilic gelling polymer is included in the pharmaceutical composition, the amount the hydrophilic gelling polymer may range from about 0.1% to about 40% by weight of the pharmaceutical composition. In certain embodiments, the amount the hydrophilic gelling polymer may range from about 0.1% to about 5%, from about 5% to about 10%, from about 10% to about 20%, or from about 20% to about 40% by weight of the pharmaceutical composition. In exemplary embodiments in which the hydrophilic gelling polymer is included, the amount of the hydrophilic gelling polymer included in the pharmaceutical composition may range from about 5% to about 20% by weight of the pharmaceutical composition.

Clay mineral. The optional modifying agent may be a clay mineral. As used herein, a "clay mineral" refers to a hydrated aluminum phyllosilicate or a hydrated magnesium silicate. In general, clay minerals comprise small insoluble particles. The clay mineral may be absorbent and/or adsorbent. Inclusion of a clay mineral may not only increase the tensile strength of the pharmaceutical composition, but the clay mineral also may adsorb the API when the pharmaceutical composition is in contact with a small volume of a suitable solvent. Additionally, the clay mineral may provide a visual deterrent to tampering with the pharmaceutical composition because the small clay particles form a cloudy suspension when in contact with a small volume of a suitable solvent.

Non-limiting examples of suitable clay minerals include talc, bentonites (such as sodium bentonite or calcium bentonite), kaolinites, nontronites, montmorillonites, pyrophyllites, saponites, sauconites, vermiculites, and combinations thereof. In a preferred embodiment, the clay mineral may be sodium bentonite. In embodiments in which the clay mineral is present in the pharmaceutical composition, the amount of the clay mineral may range from about 0.1% to about 5% by weight of the pharmaceutical composition. In various embodiments, the amount of the clay mineral may range from about 0.1% to about 0.3%, from about 0.3% to about 1%, or from about 1% to about 5% by weight of the pharmaceutical composition.

Super-disintegrant. The optional modifying agent may be a super-disintegrant. A super-disintegrant may facilitate the gelling kinetics of the pharmaceutical composition when it is in contact with a small volume of a suitable solvent, without affecting the extended release properties of the pharmaceutical composition. Non-limiting examples of suitable super-disintegrants include crospovidone, croscarmellose sodium, colloidal silicon dioxide, sodium starch glycolate, and low substituted hydroxypropyl cellulose. In one embodiment, the super-disintegrant may be crospovidone.

In embodiments in which the pharmaceutical composition includes a super-disintegrant, the amount of the super-disintegrant may range from about 0.1% to about 10% by weight of the pharmaceutical composition. In certain embodiments, the amount of the super-disintegrant may range from about 0.1% to about 0.3%, from about 0.3% to about 1%, from about 1% to about 3%, or from about 3% to about 10% by weight of the pharmaceutical composition. In exemplary embodiments, the amount of super-disintegrant included in the pharmaceutical composition may range from about 0.25% to about 3% by weight of the pharmaceutical composition.

Alkalizing agent. The optional modifying agent may be an alkalizing agent. Inclusion of an alkalizing agent may facilitate the gelling kinetics of the hydrophilic elastomer when the pharmaceutical composition is in contact with a small volume of a suitable solvent. Thus, the presence of the alkalizing agent may provide additional abuse deterrent features to the pharmaceutical composition. Non-limiting examples of suitable alkalizing agents include di- and tri-basic phosphate salts (e.g., sodium or potassium phosphate dibasic, or sodium or potassium phosphate tribasic), bicarbonate salts (e.g., sodium or potassium bicarbonate), carbonate salts (e.g., sodium or potassium carbonate), and combinations thereof. In exemplary embodiments, the alkalizing agent may be potassium phosphate dibasic.

In embodiments in which the alkalizing agent is included in the pharmaceutical compositions, the amount of the alkalizing agent may range from about 0.1% to about 3% by weight of the pharmaceutical composition. In various embodiments, the amount of the alkalizing agent may range from about 0.1% to about 0.3%, from about 0.3% to about 1%, or from about 1% to about 3% by weight of the pharmaceutical composition.

Lubricant. The optional modifying agent may be a lubricant, which facilitates preparation of solid dosage forms of the pharmaceutical composition. Non-limiting examples of suitable lubricants include magnesium stearate, calcium stearate, zinc stearate, colloidal silicon dioxide, hydrogenated vegetable oils, sterotex, polyoxyethylene monostearate, polyethylene glycol, sodium stearyl fumarate, sodium benzoate, sodium lauryl sulfate, magnesium lauryl sulfate, and light mineral oil. In exemplary embodiments, the lubricant may be magnesium stearate or colloidal silicon dioxide.

In embodiments in which the lubricant is included in the pharmaceutical composition, the amount of the lubricant may range from about 0.1% to about 3% by weight of the pharmaceutical composition. In various embodiments, the amount of the lubricant may range from about 0.1% to about 0.3%, from about 0.3% to about 1%, or from about 1% to about 3% by weight of the pharmaceutical composition. In exemplary embodiments, the amount of the lubricant may be about 1% by weight of the pharmaceutical composition.

(v) API

The pharmaceutical composition disclosed also comprises at least one API or salt thereof. Suitable APIs include, without limit, opioid analgesic agents (e.g., adulmine, alfentanil, allocryptopine, allylprodine, alphaprodine, anileridine, aporphine, benzylmorphine, berberine, bicuculine, bicucine, bezitramide, buprenorphine, bulbocaprine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tapentadol, tilidine, and tramadol); non-opioid analgesic agents (e.g., acetylsalicylic acid, acetaminophen, paracetamol, ibuprofen, ketoprofen, indomethacin, diflunisol, naproxen, ketorolac, dichlophenac, tolmetin, sulindac, phenacetin, piroxicam, and mefamanic acid); anti-inflammatory agents (e.g., glucocorticoids such as alclometasone, fluocinonide, methylprednisolone, triamcinolone and dexamethasone; non-steroidal anti-inflammatory agents such as celecoxib, deracoxib, ketoprofen, lumiracoxib, meloxicam, parecoxib, rofecoxib, and valdecoxib); antitussive agents (e.g., dextromethorphan, codeine, hydrocodone, caramiphen, carbetapentane, and dextromethorphan); antipyretic agents (e.g., acetylsalicylic acid and acetaminophen); antibiotic agents (e.g., aminoglycosides such as, amikacin, gentamicin, kanamycin, neomycin, netilmicin, streptomycin, and tobramycin; carbecephem such as loracarbef; carbapenems such as certapenem, imipenem, and meropenem; cephalosporins such as cefadroxil cefazolin, cephalexin, cefaclor, cefamandole, cephalexin, cefoxitin, cefprozil, cefuroxime, cefixime, cefdinir, cefditoren, cefoperazone, cefotaxime, cefpodoxime, ceftazidime, ceftibuten, ceftizoxime, and ceftriaxone; macrolides such as azithromycin, clarithromycin, dirithromycin, erythromycin, and troleandomycin; monobactam; penicillins such as amoxicillin, ampicillin, carbenicillin, cloxacillin, dicloxacillin, nafcillin, oxacillin, penicillin G, penicillin V, piperacillin, and ticarcillin; polypeptides such as bacitracin, colistin, and polymyxin B; quinolones such as ciprofloxacin, enoxacin, gatifloxacin, levofloxacin, lomefloxacin, moxifloxacin, norfloxacin, ofloxacin, and trovafloxacin; sulfonamides such as mafenide, sulfacetamide, sulfamethizole, sulfasalazine, sulfisoxazole, and trimethoprim-sulfamethoxazole; tetracyclines such as demeclocycline, doxycycline, minocycline, and oxytetracycline); antimicrobial agents (e.g., ketoconazole, amoxicillin, cephalexin, miconazole, econazole, acyclovir, and nelfinavir); antiviral agents (e.g., acyclovir, gangciclovir, oseltamivir, and relenza); steroids (e.g., estradiol, testosterone, cortisol, aldosterone, prednisone, and cortisone); amphetamine stimulant agents (e.g., amphetamine and amphetamine-like drugs); non-amphetamine stimulant agents (e.g., methylphenidate, nicotine, and caffeine); laxative agents (e.g., bisacodyl, casanthranol, senna, and castor oil); anti-nausea agents (e.g., dolasetron, granisetron, ondansetron, tropisetron, meclizine, and cyclizine); anorexic agents (e.g., fenfluramine, dexfenfluramine, mazindol, phentermine, and aminorex); antihistaminic agents (e.g., phencarol, cetirizine, cinnarizine, ethamidindole, azatadine, brompheniramine, hydroxyzine, and chlorpheniramine); antiasthmatic agents (e.g., zileuton, montelukast, omalizumab, fluticasone, and zafirlukast); antidiuretic agents (e.g., desmopressin, vasopressin, and lypressin); antimigraine agents (e.g., naratriptan, frovatriptan, eletriptan, dihydroergotamine, zolmitriptan, almotriptan, and sumatriptan); antispasmodic agents (e.g., dicyclomine, hyoscyamine, and peppermint oil); antidiabetic agents (e.g., methformin, acarbose, miglitol, pioglitazone, rosiglitazone, nateglinide, repaglinide, mitiglinide, saxagliptin, sitagliptine, vildagliptin, acetohexamide, chlorpropamide, gliclazide, glimepiride, glipizide, glyburide, tolazamide, and tolbutamide); respiratory agents (e.g., albuterol, ephedrine, metaproterenol, and terbutaline); sympathomimetic agents (e.g., pseudoephedrine, phenylephrine, phenylpropanolamine, epinephrine, norepinephrine, dopamine, and ephedrine); H2 blocking agents (e.g., cimetidine, famotidine, nizatidine, and ranitidine); antihyperlipidemic agents (e.g., clofibrate, cholestyramine, colestipol, fluvastatin, atorvastatin, genfibrozil, lovastatin, niacin, pravastatin, fenofibrate, colesevelam, and simvastatin); antihypercholesterol agents (e.g., lovastatin, simvastatin, pravastatin, fluvastatin, atorvastatin, cholestyramine, colestipol, colesevelam, nicotinic acid, gemfibrozil, and ezetimibe); cardiotonic agents (e.g., digitalis, ubidecarenone, and dopamine); vasodilating agents (e.g., nitroglycerin, captopril, dihydralazine, diltiazem, and isosorbide dinitrate); vasoconstricting agents (e.g., dihydroergotoxine and dihydroergotamine); anticoagulants (e.g., warfarin, heparin, and Factor Xa inhibitors); sedative agents (e.g., amobarbital, pentobarbital, secobarbital, clomethiazole, diphenhydramine hydrochloride, and alprazolam); hypnotic agents (e.g., zaleplon, zolpidem, eszopiclone, zopiclone, chloral hydrate, and clomethiazole); anticonvulsant agents (e.g., lamitrogene, oxycarbamezine, phenytoin, mephenytoin, ethosuximide, methsuccimide, carbamazepine, valproic acid, gabapentin, topiramate, felbamate, and phenobarbital); muscle relaxing agents (e.g., baclofen, carisoprodol, chlorzoxazone, cyclobenzaprine, dantrolene sodium, metaxalone, orphenadrine, pancuronium bromide, and tizanidine); antipsychotic agents (e.g., phenothiazine, chlorpromazine, fluphenazine, perphenazine, prochlorperazine, thioridazine, trifluoperazine, haloperidol, droperidol, pimozide, clozapine, olanzapine, risperidone, quetiapine, ziprasidone, melperone, and paliperidone); antianxiolitic agents (e.g., lorazepam, alprazolam, clonazepam, diazepam, buspirone, meprobamate, and flunitrazepam); antihyperactive agents (e.g., methylphenidate, amphetamine, and dextroamphetamine); antihypertensive agents (e.g., alpha-methyldopa, chiortalidone, reserpine, syrosingopine, rescinnamine, prazosin, phentolamine, felodipine, propanolol, pindolol, labetalol, clonidine, captopril, enalapril, and lisonopril); anti-neoplasia agents (e.g., taxal, actinomycin, bleomycin A2, mitomycin C, daunorubicin, doxorubicin, epirubicin, idarubicin, and mitoxantrone); soporific agents (e.g., zolpidem tartrate, eszopiclone, ramelteon, and zaleplon); tranquilizer agents (e.g., alprazolam, clonazepam, diazepam, flunitrazepam, lorazepam, triazolam, chlorpromazine, fluphenazine, haloperidol, loxapine succinate, perphenazine, prochlorperazine, thiothixene, and trifluoperazine); decongestant agents (e.g., ephedrine, phenylephrine, naphazoline, and tetrahydrozoline); beta blockers (e.g., levobunolol, pindolol, timolol maleate, bisoprolol, carvedilol, and butoxamine); alpha blockers (e.g., doxazosin, prazosin, phenoxybenzamine, phentolamine, tamsulosin, alfuzosin, and terazosin); non-steroidal hormones (e.g., corticotropin, vasopressin, oxytocin, insulin, oxendolone, thyroid hormone, and adrenal hormone); erectile disfunction improvement agents; herbal agents (e.g., glycyrrhiza, aloe, garlic nigella sativa, rauwolfia, St John's wort, and valerian); enzymes (e.g., lipase, protease, amylase, lactase, lysozyme, and urokinase); humoral agents (e.g., prostaglandins, natural and synthetic, for example, PGE1, PGE2alpha, PGF2alpha, and the PGE1 analog misoprostol); psychic energizers (e.g., 3-(2-aminopropy)indole and 3-(2-aminobutyl)indole); nutritional agents; essential fatty acids; non-essential fatty acids; vitamins; minerals; and combinations thereof.

Any of the above-mentioned APIs may be incorporated in the pharmaceutical composition described herein in any suitable form, such as, for example, as a pharmaceutically acceptable salt, uncharged or charged molecule, molecular complex, solvate or hydrate, prodrug, and, if relevant, isomer, enantiomer, racemic mixture, and/or mixtures thereof. Furthermore, the API may be in any of its crystalline, semi-crystalline, amorphous, or polymorphous forms.

In one embodiment, the API present in the pharmaceutical composition may have a potential for abuse. For example, the API may be an opioid analgesic agent, a stimulant agent, a sedative agent, a hypnotic agent, an antianxiolitic agent, or a muscle relaxing agent.

In another embodiment, the API present in the pharmaceutical composition may be a combination of an opioid analgesic and a non-opioid analgesic. Suitable opioid and non-opioid analgesics are listed above.

In exemplary embodiments, the API in the pharmaceutical composition may be an opioid analgesic. Exemplary opioid analgesics include oxycodone, oxymorphone, hydrocodone, hydromorphone, codeine, and morphine. In an exemplary embodiment, the API may be oxycodone hydrochloride. In another exemplary embodiment, the API may be oxymorphone hydrochloride.

The amount of API in the pharmaceutical composition can and will vary depending upon the active agent. In embodiments in which the API is an opioid analgesic, the amount of opioid in the pharmaceutical composition may range from about 2 mg to about 160 mg. In various embodiments, the amount of opioid in the pharmaceutical composition may range from about 2 mg to about 10 mg, from about 10 mg to about 40 mg, from about 40 mg to about 80 mg, or from about 80 mg to about 160 mg. In certain embodiments, the amount of opioid in the pharmaceutical composition may be about 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 45 mg, 50 mg, 60 mg, 70 mg, 80 mg, 100 mg, 120 mg, 140 mg, or 160 mg.

In embodiments in which the opioid is oxycodone hydrochloride, the total amount of oxycodone hydrochloride present in the pharmaceutical composition may range from about 2 mg to about 80 mg. In certain embodiments, the amount of oxycodone hydrochloride present in the pharmaceutical composition may range from about 2 mg to about 10 mg, from about 10 mg to about 30 mg, or from about 30 mg to about 80 mg. In preferred embodiments, the amount of oxycodone hydrochloride present in the pharmaceutical composition may be about 5 mg, about 10 mg, about 15 mg, about 20 mg, about 30 mg, about 40 mg, about 60 mg, or about 80 mg.

In embodiments in which the opioid is oxymorphone hydrochloride, the total amount of oxymorphone hydrochloride present in the pharmaceutical composition may range from about 2 mg to about 80 mg. In certain embodiments, the amount of oxymorphone hydrochloride present in the pharmaceutical composition may range from about 2 mg to about 10 mg, from about 10 mg to about 30 mg, or from about 30 mg to about 80 mg. In preferred embodiments, the amount of oxymorphone hydrochloride present in the pharmaceutical composition may be about 5 mg, about 10 mg, about 20 mg, about 30 mg, or about 40 mg.

(vi) Optional Excipients

In various embodiments, the pharmaceutical composition disclosed herein may further comprise at least one additional pharmaceutically acceptable excipient. Non-limiting examples of suitable excipients include binders, fillers, diluents, antioxidants, chelating agents, flavoring agents, coloring agents, taste masking agents, and combinations thereof.

In one embodiment, the excipient may be a binder. Suitable binders include, but are not limited to, starches, pregelatinized starches, gelatin, polyvinylpyrrolidone, cellulose, methyl cellulose, sodium carboxymethyl cellulose, ethyl cellulose, polyacrylamides, polyvinyloxoazolidone, polyvinylalcohols, C12-C18 fatty acid alcohol, polyethylene glycol, polyols, saccharides, oligosaccharides, polypeptides, peptides, and combinations thereof.

In another embodiment, the excipient may be a filler. Suitable fillers include carbohydrates, inorganic compounds, and polyvinylpyrrolidone. For example, the filler may be calcium sulfate, calcium phosphate, calcium silicate, microcrystalline cellulose, starch, modified starches, lactose, sucrose, mannitol, sorbitol, or combinations thereof.

In another embodiment, the excipient may include a diluent. Non-limiting examples of diluents suitable for use include pharmaceutically acceptable saccharides such as sucrose, dextrose, lactose, microcrystalline cellulose, fructose, xylitol, and sorbitol; polyhydric alcohols; starches; pre-manufactured direct compression diluents; and mixtures of any of the foregoing.

In yet another embodiment, the excipient may be an antioxidant. Suitable antioxidants include, without limit, ascorbyl palmitate, butylated hydroxyanisole, a mixture of 2 and 3 tertiary-butyl-4-hydroxyanisole, butylated hydroxytoluene, sodium isoascorbate, dihydroguaretic acid, potassium sorbate, sodium bisulfate, sodium metabisulfate, sorbic acid, potassium ascorbate, vitamin E, 4-chloro-2,6-ditertiarybutylphenol, alphatocopherol, and propylgallate.

In an alternate embodiment, the excipient may be a chelating agent. Non-limiting examples of suitable chelating agents include ethylenediamine tetracetic acid (EDTA) and its salts, N-(hydroxy-ethyl)ethylenediaminetriacetic acid, nitrilotriacetic acid (NIA), ethylene-bis(oxyethylene-nitrilo) tetraacetic acid, 1,4,7,10-tetraazacyclodo-decane-N,N', N'',N'''-tetraacetic acid, 1,4,7,10-tetraaza-cyclododecane-N, N',N''-triacetic acid, 1,4,7-tris(carboxymethyl)-10-(2'-hydroxypropyl)-1,4,7,10-tetraazocyclodecane, 1,4,7-triazacyclonane-N,N',N''-triacetic acid, 1,4,8,11-tetraazacyclotetradecane-N,N', N'',N'''-tetraacetic acid; diethylenetriamine-pentaacetic acid (DTPA), ethylenedicysteine, bis (aminoethanethiol)carboxylic acid, triethylenetetraamine-hexaacetic acid, and 1,2-diaminocyclohexane-N,N,N',N'-tetraacetic acid.

In a further embodiment, the excipient may be a flavoring agent. Flavoring agents may be chosen from synthetic flavor oils and flavoring aromatics and/or natural oils, extracts from plants, leaves, flowers, fruits, and combinations thereof.

In still another embodiment, the excipient may be a coloring agent. Suitable color additives include food, drug and cosmetic colors (FD&C), drug and cosmetic colors (D&C), or external drug and cosmetic colors (Ext. D&C).

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

The amount of excipient or excipients included in the pharmaceutical composition can and will vary depending upon the identity and amounts of the components of the pharmaceutical composition as detailed above.

(vii) Optional Film Coating

In some embodiments, the pharmaceutical composition may further comprise an optional film coating. Typically, the film coating comprises at least one water-soluble polymer, and the film coating does not affect the extended release or abuse deterrent properties of the pharmaceutical composition. The film coating may provide moisture protection, enhanced appearance, increased mechanical integrity, improved swallowability, improved taste, and/or masking of odors.

Film coatings are well known in the art, e.g., some are commercially available, e.g., under the tradename OPADRY®. Typically, a film coating comprises at least one water-soluble polymer and at least one plasticizer. Non-limiting examples of suitable polymers include hydroxypropylmethyl cellulose, hydroxypropyl cellulose, hydroxypropylethyl cellulose, ethyl cellulose, methyl cellulose, cellulose acetate phthalate, microcrystalline cellulose and carrageenan, acrylic polymers, polyvinyl alcohol, anionic and cationic polymers of methacrylic acid, copolymers of methacrylates, copolymers of acrylates and methacrylates, copolymers of ethacrylate and methyl methacrylate, polyvinylacetate phthalate, and shellac. Examples of suitable plasticizers include, without limit, triethyl citrate (TEC), acetyltriethyl citrate (ATEC), acetyl tri-n-butyl citrate (ATBC), dibutyl sebacate, diethyl phthalate, and triacetin. The film coating may optionally comprise additional agents such as a coloring agent, a filler, a flavoring agent, a taste-masking agent, a surfactant, an anti-tacking agent, and/or an anti-foaming agent. Suitable examples of these agents are well known in the art and/or are detailed above.

(b) Dosage Forms

The physical form of the pharmaceutical composition disclosed herein can and will vary. In general, the pharmaceutical composition is a solid dosage form. The solid dosage form may be one of various solid dosage units. Non-limiting examples of suitable solid dosage units include tablets, compacts, pellets, caplets, pills, and capsules. Such dosage units may be prepared using conventional methods known to those in the field of pharmaceutical formulation and described in the pertinent texts, e.g., in Gennaro, A. R., editor. "Remington: The Science & Practice of Pharmacy", 21st ed., Williams & Williams, and in the "Physician's Desk Reference", 2006, Thomson Healthcare. In general, the solid dosage form is formulated for oral administration.

In exemplary embodiments, the solid dosage unit may be a tablet. Non-limiting types of tablets include coated tablets, uncoated tablets, compressed tablets, compacted tablets, molded tablets, layered tablets, bilayer tablets, extruded tablets, multiparticle tablets, monolithic tablets, and matrix tablets. In exemplary embodiments, the pharmaceutical composition may be a solid dosage form comprising a tablet.

In embodiments in which the solid dosage form is a tablet, the tablet generally has a friability of no greater than about 1.0%. In certain embodiments, the tablet may have a friability of less than about 1.0%, less than about 0.5%, less than about 0.3%, less than about 0.2%, less than about 0.1%, less than about 0.05%, or less than about 0.01%. In exemplary embodiments, the tablet has a friability of zero.

(c) In Vitro Release Properties of the Composition

The solid dosage pharmaceutical composition disclosed herein is formulated such that the API in the composition is released over an extended period of time. For example, the total amount of API in the pharmaceutical composition may be released over a period of about 6 hours, over a period of about 12 hours, over a period of about 18 hours, or over a period of about 24 hours. In exemplary embodiments, the total amount of the API in the pharmaceutical composition may be released within about 8 hours to about 12 hours.

The in vitro dissolution of the API from the solid dosage pharmaceutical composition disclosed herein may be measured using an approved USP procedure. For example, dissolution may be measured using an USP approved Type 2 paddle apparatus, at a paddle speed of 50 rpm or 100 rpm, and a constant temperature of 37±0.5° C. The dissolution test may be performed in the presence of 500 mL, 900 mL, or 1,000 mL of a suitable dissolution medium (e.g., having a pH from 1.0 to 6.8). Non-limiting examples of suitable dissolution media include water, phosphate buffer (pH 6.8), acetate buffer (pH 4.5), and 0.1N HCl.

In various embodiments, the in vitro release of the API from the pharmaceutical composition is such that no more than about 50%, 60%, 70%, 80%, 90% or 95% of the API is released within about 6 hours. In additional embodiments, no more than about 80% of the API is released within about 6 hours. In still another embodiment, no more than about 50%, 60%, 70%, 80%, 90% or 95% of the API is released within about 8 hours.

(d) Abuse Deterrent Properties of the Composition

The solid dosage pharmaceutical compositions disclosed herein also have abuse deterrent features. The combination of the plasticized hydrophilic plastomers and plasticized hydrophilic elastomers imparts sufficient mechanical integrity (i.e., strength, hardness, elasticity, etc.) to the composition such that it is resistant to crushing, grinding, cutting, or pulverizing to form a powder comprising small particles. Additionally, the composition comprises gelling polymers such that the composition forms a viscous mixture or gel when in contact with a small volume of a suitable solvent.

The mechanical integrity of the solid dosage pharmaceutical composition may be assessed by measuring the particle size distribution after crushing, grinding, or pulverizing the composition in a suitable apparatus for a specified period of time The composition may be crushed, ground, or pulverized in a pill crusher, a tablet grinder, a ball mill, a co-mill, a high-shear mill, a coffee grinder, a blender, a hammer, or another apparatus to reduce particle size. In various embodiments in which the composition is subjected to 12 minutes of grinding or milling to form particles, more than 20%, 30%, 40%, 50%, 60%, 70%, 80%, 90%, or 95% of the particles may have an average diameter of at least about 250 microns. In further embodiments, in which the composition is subjected to 12 minutes of grinding or milling to form particles, more than 20%, 30%, 40%, 50%, 60%, 70%, 80%, 90%, or 95% of the particles may have an average diameter of at least about 500 microns. Because the pharmaceutical composition disclosed herein is resistant to forming a fine powder, it deters abuse by inhalation.

Alternatively, the mechanical integrity of the pharmaceutical composition may be accessed by measuring the breaking point or the breaking strength of the solid dosage composition. The breaking strength refers to the amount of applied force needed to compromise the integrity of the solid dosage form. The breaking point may be determined from a force profile of the composition. The force profile is a plot of force versus compression distance in which changes in the thickness of the solid dosage form are plotted as a function of increasing force applied to the solid dosage form (Haslam et al., Int. J. Pharmaceut., 1998, 173:233-242). The force profile may be generated using a Texture Analyzer model TA.XT. Plus (Texture Technologies Corp.), an Instron Universal Tester (Instron Engineering Corp.), or other suitable instrument. Force is applied diametrically to the solid dosage form and the compression distance is recorded. The breaking point exhibits itself as the point in the force profile plot at which the ascending line plateaus or descends in response to the application of increasing force (see FIG. 3). The breaking point may be expressed as force per compression distance.

Another method to determine the breaking point (or breaking strength) utilizes conventional hardness testers well known in the art. Appropriate models include, without limitation, Dr. Schleuniger® model 8M (Pharmatron Inc.), Varian model VK200 (Varian Medical Systems Inc.), or Sotax HT1 (Sotax Corp.). In this analysis, when the integrity of the dosage form is compromised, the instrument will stop compressing and report the force delivered to the dosage form at the breaking strength. In general, the pharmaceutical composition disclosed herein has a breaking strength of less than about 500 Newtons (N). In various embodiments, the breaking strength of the pharmaceutical composition is less than about 400 N, less than about 350 N, less than about 300 N, less than about 250 N, or less than about 200 N. As additional force is applied beyond the breaking point, the composition continues to flatten or deform, which is indicative of plastic deformation.

An additional abuse deterrent property is that the pharmaceutical composition, whether whole, flattened, or broken into large particles, forms a viscous mixture or gel when in contact with a small volume of a suitable solvent. The volume of the suitable solvent may range from about 1 mL to about 10 mL. For example, the volume may be about 2 mL, about 3 mL, about 4 mL about 5 mL, about 6 mL, about 7 mL, about 8 mL, about 9 mL, or about 10 mL. Suitable solvents include water, alcohols such as ethanol, acids such as acetic acid, fruit juice, and mixtures of any of the foregoing. The resultant gel has a high viscosity that prevents separation of the active ingredient from the viscous gel, provides a visual deterrence to injection abuse, and inhibits the gelled mixture from being drawn through an injection syringe needle. Consequently, the pharmaceutical compositions disclosed herein provide deterrence to abuse by extraction of the API and consequent injection of the extracted mixture.

(e) Exemplary Embodiments

In one exemplary embodiment, the hydrophilic plastomer comprises hydroxypropyl cellulose, hydroxypropylmethyl cellulose, and polyethylene oxide, and is present in an amount ranging from about 50% to about 80% by weight of the composition; the optional hydrophilic elastomer is present and is a carbomer present in an amount ranging from about 0.5% to about 10% by weight of the composition; the deliquescent plasticizer comprises citric acid and sorbitol, and is present in an amount ranging from about 10% to about 30% by weight of the composition; the optional lubricant is magnesium stearate; the API is chosen from oxycodone, oxymorphone, hydrocodone, hydromorphone, codeine, and morphine; and the composition is a solid dosage form.

(II) Process for Preparing Solid Dosage Pharmaceutical Compositions

Another aspect of the disclosure encompasses a process for preparing a solid dosage form of the pharmaceutical composition disclosed herein. The process comprises: (a) forming a mixture comprising at least one hydrophilic plastomer, optionally at least one hydrophilic elastomer, and at least one deliquescent plasticizer, wherein the mixture is a powder, a granulate, or a solid dosage unit; (b) humidifying the mixture of (a) to form a humidified powder, a humidified granulate, or a humidified solid dosage unit; (c) optionally forming the humidified powder or the humidified granulate into a treated solid dosage unit; (d) optionally coating the humidified solid dosage unit of (b) or the treated solid dosage unit of (c) to form a coated solid dosage unit; and (e) heating the humidified solid dosage unit of (b), the treated solid dosage unit of (c), or the coated solid dosage unit of (d) to form the solid dosage form.

(a) Forming the Mixture

The first step of the process comprises forming a mixture comprising at least one hydrophilic plastomer, optionally at least one hydrophilic elastomer, and at least one deliquescent plasticizer, which are detailed above in sections (I)(a)(i)-(iii), respectively. In some embodiments, the mixture may further comprise at least one API and/or at least one modifying agent, as detailed above in sections (i)(a)(v) and (iv), respectively.

The mixture may be a powder, a granulate, or a solid dosage unit. As mentioned above in section (I)(b), suitable solid dosage units include tablets, compacts, pellets, caplets, pills, and capsules. In some embodiments, the components of the mixture may be blended, mixed, roller compacted, milled, and/or granulated, thereby forming a blend or a granulate. All these procedures are well known in the art. In other embodiments, the blend or granulate may be formed into a solid dosage unit using techniques well known in the art.

(b) Humidifying the Mixture

The process further comprises humidifying the mixture of (a) to form a humidified powder, a humidified granulate, or a humidified solid dosage unit. During this step of the process, the partial pressure of the water vapor in the atmosphere exceeds the partial water vapor pressure of the deliquescent plasticizer such that the deliquescent plasticizer absorbs moisture from the atmosphere and forms a saturated solution. As a consequence, the mobility of the plasticizer increases such that it can incorporate into the hydrophilic plastomer and elastomer, thereby plasticizing the hydrophilic plastomer and elastomer. As detailed below in Example 5, the humidification step increases the mechanical integrity of the solid dosage form, and consequently increases the abuse deterrence of the solid dosage form of the pharmaceutical composition.

The temperature and relative humidity at which the humidification step occurs can and will vary depending mainly upon the identity of the deliquescent plasticizer. Each deliquescent plasticizer deliquesces at a particular level or range of relative humidity. For example, citric acid deliquesces at about 75% relative humidity at 25° C., and sorbitol deliquesces from about 69% to about 91% relative humidity at 25° C.

In various embodiments, the humidification step may occur at a relative humidity that ranges from about 40% to about 100% at 25° C. In some embodiments, the relative humidity may range from about 40% to about 50% at 25° C., from about 50% to about 60% at 25° C., from about 60% to about 70% at 25° C., from about 70% to about 80% at 25°

C., from about 80% to about 90% at 25° C., or from about 90% to about 100% at 25° C. In exemplary embodiments, the relative humidity during the humidification step may range from about 65% to about 85% at 25° C.

The temperature of the humidification step also may vary. In general, the humidification step may occur at a temperature ranging from about 5° C. to about 90° C. In certain embodiments, the temperature of the humidification step may range from about 5° C. to about 15° C., from about 15° C. to about 30° C., from about 30° C. to about 60° C., or from about 60° C. to about 90° C. In exemplary embodiments, the temperature of the humidification step may range from about 30° C. to about 50° C.

The duration of the humidification step can and will vary depending upon the components of the pharmaceutical composition and the humidification conditions. In general, the duration of the humidification step may range from several minutes to several hours. For example, the duration of the humidification step may range from about 10 minutes to about 1 hour, from about 1 hour to about 2 hours, or from about 2 hours to about 5 hours. In one exemplary embodiment, the duration of the humidification step may be about 2 hours.

The powder, granulate, or solid dosage form may be humidified in a pan coater unit, an oven, a humidifier, a humidification chamber, a V-blender, or other suitable apparatus known in the art.

The humidified solid dosage unit may be dried prior to the optional coating step (d). The temperature of the drying step may vary. In general, the drying step may occur at a temperature ranging from about 5° C. to about 90° C. In certain embodiments, the temperature of the optional drying step may range from about 5° C. to about 15° C., from about 15° C. to about 30° C., from about 30° C. to about 60° C., or from about 60° C. to about 90° C. In exemplary embodiments, the temperature of the drying step may range from about 30° C. to about 50° C. Optional use of nitrogen or vacuum assisted drying techniques will lower the temperature and time requirements needed to effect drying and is assumed to be included in the body of this work as obvious to someone versed in the art.

The duration of the drying step can and will vary depending upon the components of the pharmaceutical composition and the humidification conditions. In general, the duration of the drying step may range from several minutes to several hours. For example, the duration of the drying step may range from about 10 minutes to about 1 hour, from about 1 hour to about 2 hours, or from about 2 hours to about 5 hours. In one exemplary embodiment, the duration of the humidification step may be about 2 hours (c) Optionally Forming a Solid Dosage Unit In embodiments in which the mixture from step (a) comprises a powder or a granulate, the humidified powder or the humidified granulate formed during step (b) may be optionally mixed with at least one API and/or at least one modifying agent and formed into a treated solid dosage unit using procedures well known in the art.

(d) Optionally Coating the Solid Dosage Unit

The process further comprises an optional step in which the humidified solid dosage unit from step (b) or the treated solid dosage unit from step (c) is coated with a film coating to form a coated solid dosage form. Examples of suitable film coatings are detailed above in section (I)(a)(vii). The optional coating step prevents agglomeration or sticking among individual solid dosage forms and sticking between the solid dosage forms and the equipment. The film coating may be spray coated onto the solid dosage form. The spray coating system by be a bottom spray coating system, a top spray coating system, a tangential spray coating system, a pan coating system, or another suitable coating system.

(e) Heating the Solid Dosage Unit

The final step of the process comprises heating the humidified solid dosage unit from step (b), the treated solid dosage unit from step (c), or the coated solid dosage unit from step (d) to form the solid dosage form. This heating step essentially cures the hydrophilic plastomer in the solid dosage unit matrix that has a softening temperature below the selected temperature. The heating step may also remove excess moisture from the dosage unit retained from the humidification step. The solid dosage form prepared by the process disclosed herein has sufficient mechanical integrity such that it is resistant to crushing, cutting, milling, pulverizing, or other means of tampering.

In general, the heating step occurs at a temperature greater than about 50° C. For example, the humidified or treated solid dosage units may be heated to a temperature greater than about 50° C., greater than about 60° C., greater than about 70° C., greater than about 80° C., greater than about 90° C., or greater than about 100° C. In exemplary embodiments, the temperature of the heating step may range from about 60° C. to about 90° C.

The duration of the heating step can and will vary depending upon the components of the pharmaceutical composition. The duration of the heating step may range from about 10 minutes to about 10 hours. In general, the higher the temperature, the shorter the duration of time. For example, the solid dosage unit may be heated to a temperature of about 80° C. for about 3 hours, or the solid dosage unit may be heated to a temperature of about 90° C. for about 1 hour.

(f) Iterations of the Process

Persons skilled in the art will appreciate that different components of the pharmaceutical composition may be introduced at various points during the process for preparing a solid dosage form of the pharmaceutical composition. Table A lists non-limiting examples of various iterations of the process.

TABLE A

Possible Iterations

| # | Details of Process* |
|---|---|
| 1 | granulate a + b + c + d → add e → form tablet → humidify → (optional coat) → heat |
| 2 | granulate a + b + c + d + e → form tablet → humidify → (optional coat) → heat |
| 3 | granulate a + b + c + d → humidify → add e → form tablet → (optional coat) → heat |
| 4 | granulate d + b + c → add e → form tablet → humidify → (optional coat) → heat |
| 5 | granulate d + b + c + e → form tablet → humidify → (optional coat) → heat |
| 6 | granulate d + b + c → humidify → add e → form tablet → (optional coat) → heat |
| 7 | granulate d + f + b + c → add e → form tablet → humidify → (optional coat) → heat |
| 8 | granulate d + f + b + c + e → form tablet → humidify → (optional coat) → heat |
| 9 | granulate d + f + b + c → humidify → add e → form tablet → (optional coat) → heat |
| 10 | blend d + f + b + c + e → form tablet → humidify → (optional coat) → heat |
| 11 | blend d + f + b + c + e → humidify → form tablet → (optional coat) → heat |

TABLE A-continued

Possible Iterations

| # | Details of Process* |
|---|---|
| 12 | blend d + f + b + c → humidify → add e → form tablet → (optional coat) → heat |
| 13 | blend a + b + c + d + e → form tablet → humidify → (optional coat) → heat |
| 14 | blend a + b + c + d + e → humidify → form tablet → (optional coat) → heat |
| 15 | blend a + b + c + d → humidify → add e → form tablet → (optional coat) → heat | a = co-processed mixture of sorbitol and glycerol
b = hydrophilic plastomer
c = hydrophilic elastomer
d = citric acid
e = API
f = sorbitol Definitions Compounds useful in the compositions and methods include those described herein in any of their pharmaceutically acceptable forms, including isomers such as diastereomers and enantiomers, salts, solvates, and polymorphs, as well as racemic mixtures and pure isomers of the compounds described herein, where applicable.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

The term "about," particularly in reference to a given quantity, is meant to encompass deviations of plus or minus five percent.

EXAMPLES

The following examples are included to demonstrate preferred embodiments of the invention. It should be appreciated by those of skill in the art that the techniques disclosed in the examples represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth is to be interpreted as illustrative and not in a limiting sense.

Example 1

Preparation of Prototype #1

A first prototype of the disclosed extended release (ER), abuse deterrent formulation (ADF) was prepared in which the plasticizer comprised a combination of citric acid and a co-processed mixture of sorbitol and glycerol. The co-processed plasticizer (90% sorbitol/10% glycerol) was prepared by spraying a solution of 30% glycerol/70% isopropyl alcohol onto sorbitol powder using a suitable fluid bed coating unit or low shear planetary mixer. A mixture comprising high molecular weight hydroxypropyl cellulose (25-35% w/w), carbomer (2-4% w/w), citric acid (1-10% w/w), co-processed sorbitol/glycerol (10-20% w/w) was roller compacted to an appropriate ribbon thickness. The ribbons were milled to an appropriate particle size, which were then dry blended with hydroxypropylmethyl cellulose (1-10% w/w), polyethylene oxide (15-25% w/w), and oxycodone hydrochloride (40 mg). The blend was lubricated with Mg stearate (1% w/w), and the lubricated blend was compacted into tablets using an automated press. The tablets were humidified in a pan coater with clean steam for 2 hours at 45° C. and between 65% to 99% relative humidity, cured in the pan coater at 80° C. for 3 hours, and then coated with a non-functional appearance coating.

Example 2

Preparation of Prototype #2

A second prototype of the extended release, abuse deterrent formulation was prepared in which the plasticizer comprised a combination of citric acid and sorbitol. A mixture comprising high molecular weight hydroxypropyl cellulose (25-35% w/w), carbomer (2-4% w/w), citric acid (5-15% w/w), sorbitol (1-10% w/w) was roller compacted to the appropriate ribbon thickness. The ribbons were milled to the appropriate particle size, which were then dry blended with hydroxypropylmethyl cellulose (1-10% w/w), polyethylene oxide (15-25% w/w), and oxycodone hydrochloride (40 mg). The blend was lubricated with Mg stearate (1% w/w), and the lubricated blend was compacted into tablets using an automated press. The tablets were humidified in a pan coater with clean steam for 2 hours at 45° C. and between 65% to 99% relative humidity, cured in the pan coater at 80° C. for 3 hours, and then coated with a non-functional appearance coating.

Example 3

In Vitro Release of Oxycodone from Prototypes #1 and #2

The in vitro dissolution of oxycodone from prototypes #1 and #2 was measured in 900 phosphate buffer (pH 6.8) or 0.1N HCl using an USP type 2 paddle apparatus with a paddle speed of 50 rpm and a constant temperature of 37° C.

In some instances, the tablets (n=3) were placed in sinkers to prevent flotation. Samples were removed at various time points from 0.5 to 12 hr and analyzed by HPLC for oxycodone hydrochloride. FIG. 1 presents the dissolution profiles of prototypes #1 and #2, as well as those of a reference ER, ADF oxycodone (40 mg) formulation and a reference ER, non-ADF oxycodone (40 mg) formulation. The release of oxycodone from the prototypic preparations occurred over an extended period of time (see Table 1). For example, no more than about 80% of oxycodone was released within about 4 hours and no more than about 90% of the oxycodone was released within about 6 hours.

TABLE 1

In Vitro Release of Oxycodone

| Time (hrs) | Prototype #1 (mean %) | Prototype #2 (mean %) | Reference ER, ADF (mean %) | Reference ER, non-ADF (mean %) |
|---|---|---|---|---|
| 0.5 | 25.1 | 25.5 | 18.03 | 23.77 |
| 1 | 36.0 | 36.7 | 28.80 | 37.55 |
| 2 | 51.2 | 52.1 | 45.42 | 57.28 |
| 4 | 71.6 | 72.0 | 70.24 | 82.65 |
| 6 | 86.3 | 85.1 | 85.92 | 96.27 |

TABLE 1-continued

In Vitro Release of Oxycodone

| Time (hrs) | Prototype #1 (mean %) | Prototype #2 (mean %) | Reference ER, ADF (mean %) | Reference ER, non-ADF (mean %) |
|---|---|---|---|---|
| 8 | 94.4 | 92.5 | 94.25 | 102.24 |
| 10 | 98.1 | 96.4 | 98.13 | 104.26 |
| 12 | 99.7 | 97.9 | 99.98 | 105.19 |

Example 4

Physical Properties of the Prototypic Formulations

The abuse deterrence properties of prototypes #1 and #2 were compared to those of the reference ER, ADF oxycodone formulation and the reference ER, non-ADF oxycodone formulation. For this, each tablet was flattened in a hardness tester, the flattened tablet was twisted to form a "butterfly," and the butterflied tablet was then milled in an IKA 10A mill at 1 minute intervals for up to 15 minutes total. At relevant time points, the milled tablet was analyzed for particle size distribution using a Sonic Sifter with a screen mesh size of 35 mesh (500 microns), 60 mesh (250 microns), and 120 mesh (125 microns).

Table 2 presents the percent of particles retained on each screen or passed through the 120 mesh screen for each sample after 12 minutes of milling. For both prototypes #1 and #2, more than 80% of the particles had an average diameter of greater than 500 microns, whereas for both of the reference formulations less than 10% of the particles had an average diameter of greater than 500 microns.

TABLE 2

Particle Size Distribution After 12 Minutes of Milling

| Sample | 35 Mesh (>500 microns) (% retained) | 60 Mesh (>250 microns) (% retained) | 120 Mesh (>125 microns) (% retained) | <120 Mesh (<125 microns) (% passed through) |
|---|---|---|---|---|
| Prototype #1 | 89.05 | 96.02 | 96.02 | 0 |
| Prototype #2 | 84.58 | 94.03 | 97.01 | 0 |
| Reference ER, ADF | 6.8 | 41.5 | 89.0 | 14.4 |
| Reference ER, Non-ADF | 1.2 | 3.5 | 17.4 | 82.6 |

Figure 2:
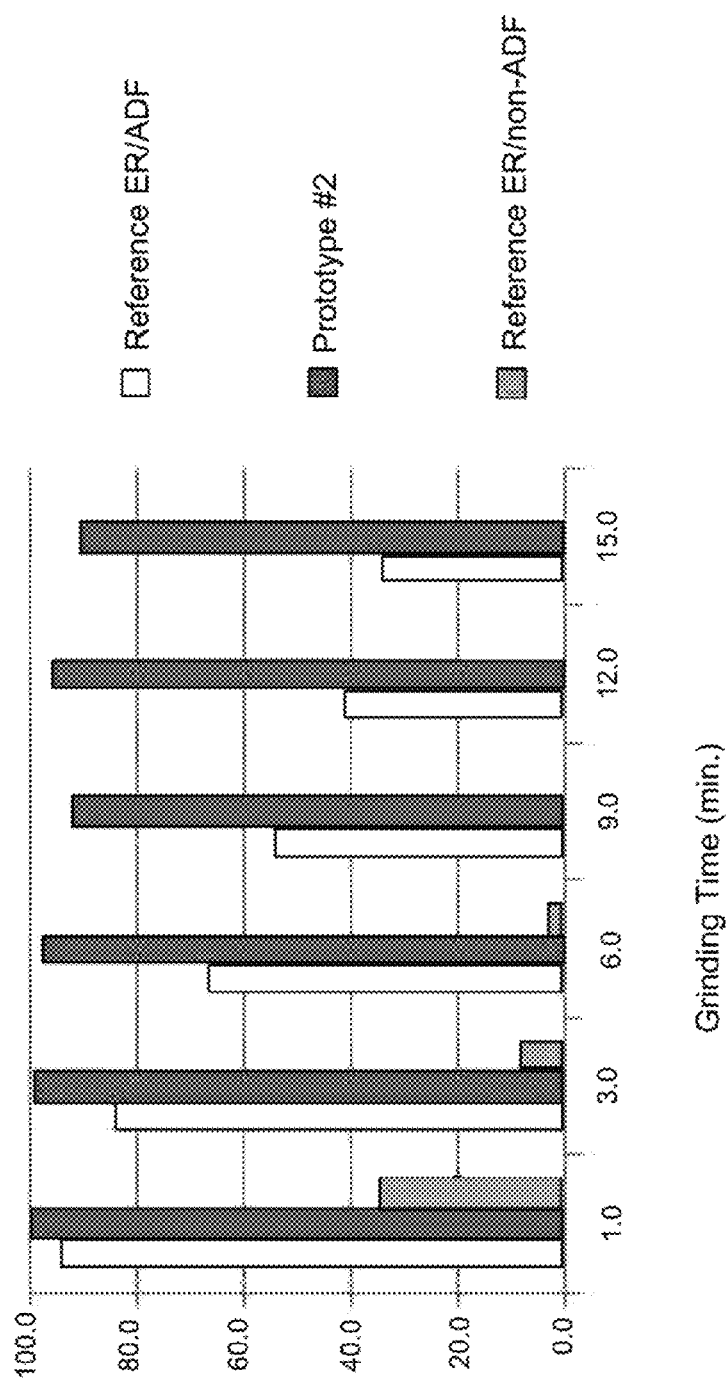
FIG. 2 illustrates abuse deterrent properties of the solid dosage form. Shown is the percent of particles retained on a 60 mesh screen (>250 microns) after various grinding times for prototype #2, a reference ER/ADF oxycodone formulation, and a reference ER/non-ADF oxycodone formulation.

FIG. 2 presents the percentage of particles retained on the 60 mesh screen as the milling time increased from 1 minute to 15 minutes for prototype #2 and the two reference formulations. Even after 15 minutes of milling, nearly 90% of the particles derived from prototype #2 had an average diameter of greater than 250 microns, whereas only about 30% of the particles derived from the reference ER, ADF had particle sizes greater than 250 microns.

Example 5

Effect of Humidifying the Prototypic Formulations

The humidification step is a transformative event in the preparation of the formulations disclosed herein. In this step, the deliquescent plasticizers adsorb water to the point of forming a saturated solution (all or in part) and increase in mobility. This allows for sufficient plasticization of the target polymers while in the blend, granulate, or tablet state. To investigate the effect of humidification, the physical properties of prototypes #1 and #2 were examined after being prepared: 1) with no humidification and curing steps; 2) with a curing step but no humidification step; and 3) with both humidification and curing steps. The physical properties of each tablet was measured by flattening the tablet in a hardness tester, measuring the thickness of the flattened tablet, butterflying the flattened tablet, and milling the butterflied tablet as described above in Example 4.

As shown in Table 3, the hardness of the tablets increased from less than about 25 kp (250N) to greater than about 85 kp (850N) when humidification was incorporated into the manufacturing process.

TABLE 3

Effect of Humidification on the Tamper Resistant Properties

| | | | Physical evaluation (% retained) | | |
|---|---|---|---|---|---|
| | Hardness Tester | | 35 Mesh | 60 Mesh | 120 Mesh |
| Prototype | Hardness (kp) | Thickness (mm) | (>500 microns) | (>250 microns) | (>125 microns) |
| 1* | 6.2 | Broke into 2 pieces | 5.21 | 16.67 | 44.27 |
| 1** | 7.8 | 7.35 | 72.68 | 90.21 | 95.88 |
| 1*** | 85.5 | 3.04 | 89.05 | 96.02 | 96.02 |
| 2* | 12.5 | Broke into 2 pieces | 6.32 | 23.56 | 61.49 |
| 2** | 23.8 | 5.91 | 88.72 | 95.38 | 95.90 |
| 2*** | 85.5 | 3.46 | 84.58 | 94.03 | 97.01 |

* = "As-is" (No humidification, no curing)
** = Cured only (No Humidification)
*** = Humidified and cured Example 6

Syringeability of the Prototypic Formulation

The combination of plasticized hydrophilic plastomers and elastomers in the pharmaceutical composition disclosed herein provides abuse deterrent properties. As demonstrated above in Examples 4 and 5, when properly plasticized, the prototypic formulation has sufficient hardness and tensile strength such that it is resistant to crushing, grinding, cutting, or pulverizing to form a powder comprising small particles. Additionally, the formulation comprises gelling polymers such that it forms a viscous mixture or gel when in contact with a small volume of a suitable solvent.

To measure syringeability, ground tablets were hydrated in 5 mL of water while stirring for 1 minute, 3 minutes, or 5 minutes. A 1 mL syringe with a 27 gauge needle connected to an appropriate instrument to measure force (Texture Analyzer) was used to pull the sample up into the syringe barrel. The amount of solution aspirated into the needle was recorded and then analyzed via HPLC to determine the oxycodone HCl content. The results for the prototypic formulation, the reference ER, ADF oxycodone formulation, and the reference ER, non-ADF oxycodone formulation are shown in Table 4. Very little oxycodone was detected in the mixtures derived from the prototype formulation.

TABLE 4

Syringeability

| Sample | Volume recovered (mL) | | | Oxycodone HCl recovered (mg) | | |
|---|---|---|---|---|---|---|
| | 1 min | 3 min | 5 min | 1 min | 3 min | 5 min |
| Prototype Formulation | 1 | 0.66 | 0.46 | 0.13 | 0.17 | 0.05 |
| Reference ER, ADF | 1 | 0.65 | 0.4 | 1.74 | 1.58 | 0.72 |
| Reference ER, Non-ADF | 0.05 | 0.1 | 0.02 | 2.53 | 1.38 | 1.2 |

Another method for testing the injectabilty of a pharmaceutical composition is to determine the amount of freely soluble drug present in small volumes regardless of polymer entrapment. In this test, whole tablets, or tablets cut into 16 pieces were hydrated with 2 mL, 5 mL or 10 mL of water and the mixture was stirred for 5 min, 10 min, or 30 min. The solution was then back loaded into a syringe stuffed with ~225 mg of cotton at the syringe tip and expelled to simulate common filtering methods. The expelled solution (regardless of viscosity) was analyzed for oxycodone content. The results for the prototypic formulation, the reference ER, ADF oxycodone formulation, and the reference ER, non-ADF oxycodone formulation are shown in Tables 5, 6, and 7.

TABLE 5

% Oxycodone extracted in 2 mL water

| | | Stirring time | | |
|---|---|---|---|---|
| Sample | Type of tablet | 5 min | 10 min | 30 min |
| Prototype Formulation | Whole Tablet | 6.3 | 8.2 | 12.7 |
| | 4 Piece Cut | 9.7 | 12.8 | 16.8 |
| Reference ER, ADF | Whole Tablet | 4 | 4.8 | 7.9 |
| | 4 Piece Cut | 5.7 | 7.2 | 10.6 |
| Reference ER, Non-ADF | Whole Tablet | 4.6 | 6.8 | 11.8 |
| | 4 Piece Cut | 8 | 12.3 | 13.4 |

TABLE 6

% Oxycodone extracted in 5 mL water

| | | Stirring time | | |
|---|---|---|---|---|
| Sample | Type of tablet | 5 min | 10 min | 30 min |
| Prototype Formulation | Whole Tablet | 8.9 | 14 | 32.7 |
| | 4 Piece Cut | 14.8 | 18.1 | 39.3 |
| Reference ER, ADF | Whole Tablet | 5 | 6.9 | 13.5 |
| | 4 Piece Cut | 7.9 | 13.3 | 23.8 |
| Reference ER, Non-ADF | Whole Tablet | 6.4 | 10.4 | 18.4 |
| | 4 Piece Cut | 12.7 | 17.8 | 33.2 |

TABLE 7

% Oxycodone extracted in 10 mL water

| | | Stirring time | | |
|---|---|---|---|---|
| Sample | Type of tablet | 5 min | 10 min | 30 min |
| Prototype Formulation | Whole Tablet | 9.3 | 14.7 | 32 |
| | 4 Piece Cut | 14.9 | 21.2 | 43.3 |
| Reference ER, ADF | Whole Tablet | 5.5 | 7.9 | 16.5 |
| | 4 Piece Cut | 8.3 | 10.6 | 28.1 |
| Reference ER, Non-ADF | Whole Tablet | 7.2 | 10.8 | 21.2 |
| | 4 Piece Cut | 12.8 | 21.9 | 36.7 |

Example 7

Preparation of Prototype #3

A third prototype of the disclosed formulation was prepared. A mixture comprising high molecular weight hydroxypropyl cellulose (15-25% w/w), hydroxypropylmethyl cellulose (5-15% w/w), oxycodone hydrochloride (10-80 mg), and Mg stearate (0.1-0.4% w/w) was roller compacted to the appropriate ribbon thickness. The ribbons were milled to the appropriate particle size, which were then dry blended with carbomer (1-4% w/w), polyethylene oxide (20-50% w/w), citric acid (5-15% w/w), and sorbitol (1-10% w/w). The blend was lubricated with Mg stearate (total of 1% w/w in overall formulation), and the lubricated blend was compacted into tablets (250 mg) using an automated press. The tablets were humidified in a pan coater with clean steam for 2 hours at 30-50° C. and between 65% to 99% relative humidity, dried at 20-60° C. for 2 hours, coated, and cured in a pan coater at 80° C. for 3 hours.

Example 8

Force Profile of Prototypic #3

Figure 3:
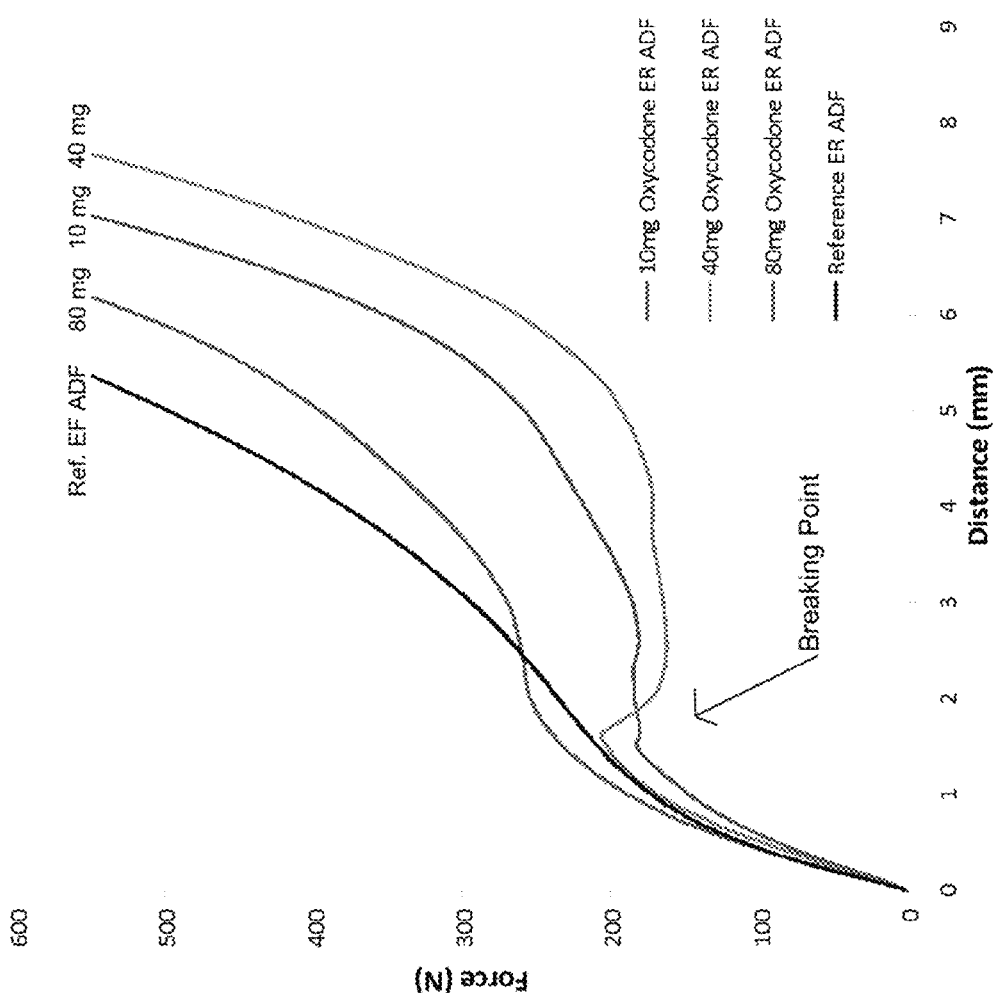
FIG. 3 presents the force profile of the solid dosage form. Plotted is the force (in Newtons) applied and the distance (in mm) compressed for tablets of three strengths of formulation prototype #3 and a reference ER/AFD oxycodone formulation. The breaking point refers to the point at which the force profile line deflects or plateaus.

The breaking point of the tablets prepared in Example 7 was determined using a Texture Analyzer model TA.XT. Plus (Texture Technologies Corp.). Force was applied diametrically to each tablet and the compression distance was recorded. As shown in FIG. 3, each tablet exhibited a specific breaking point, which was generally less than about 300 N.

Example 9

Oxymorphone Formulation

A prototype of the disclosed formulation was prepared using oxymorphone HCl as the active pharmaceutical ingredient and tested for abuse deterrence. A mixture comprising high molecular weight hydroxypropyl cellulose (15-25% w/w), hydroxypropylmethyl cellulose (5-15% w/w) and oxymorphone hydrochloride (5-40 mg), and Mg stearate (0.1-0.4% w/w) was roller compacted to the appropriate ribbon thickness. The ribbons were milled to the appropriate particle size, which were then dry blended with carbomer (1-4% w/w), polyethylene oxide (20-50% w/w), citric acid (5-15% w/w), and sorbitol (1-10% w/w). The blend was lubricated with Mg stearate (total of 1% w/w in overall formulation), and the lubricated blend was compacted into tablets using an automated press. The tablets were humidified in a pan coater with clean steam for 2 hours at 30-50°

C. and between 65% to 99% relative humidity, dried at 20-60° C. for 2 hours, coated, and cured at 80° C. for 3 hours.

What is claimed is:

1. A pharmaceutical composition comprising at least one active pharmaceutical ingredient (API) or a pharmaceutically acceptable salt thereof, at least one hydrophilic plastomer, at least one hydrophilic elastomer chosen from a carbomer, a polycarbophil, or a combination thereof, and at least one deliquescent plasticizer chosen from an organic acid, a sugar alcohol, a co-processed mixture of (i) an organic acid and/or a sugar alcohol and (ii) a liquid plasticizer, or a combination thereof, wherein the pharmaceutical composition is a solid dosage form prepared by a process comprising:
   (a) forming a mixture comprising the at least one API or pharmaceutically acceptable salt thereof, the at least one hydrophilic plastomer, the at least one hydrophilic elastomer, and the at least one deliquescent plasticizer, wherein the mixture is a powder, a granulate, or a solid dosage unit;
   (b) humidifying the mixture of (a) to form a humidified powder, a humidified granulate, or a humidified solid dosage unit, wherein the humidifying occurs at a temperature and at a relative humidity such that the deliquescent plasticizer undergoes deliquescence;
   (c) optionally forming the humidified powder or the humidified granulate of (b) into a treated solid dosage unit;
   (d) optionally coating the humidified solid dosage unit of (b) or the treated solid dosage unit of (c) to form a coated solid dosage unit; and
   (e) heating the humidified solid dosage unit of (b), the treated solid dosage unit of (c), or the coated solid dosage unit of (d) to form the solid dosage form of the pharmaceutical composition.

2. The pharmaceutical composition of claim 1, wherein the composition provides extended release of the API and has abuse deterrent properties.

3. The pharmaceutical composition of claim 1, wherein the at least one hydrophilic plastomer is chosen from a cellulose ether, a polyalkylene oxide, a polyalkylene glycol, a polyolefinic alcohol, a polyvinyl lactam, a polycarboxylic acid, a polysaccharide, a polypeptide, or a combination thereof, and is present in an amount from about 10% to about 90% by weight of the pharmaceutical composition.

4. The pharmaceutical composition of claim 3, wherein the at least one hydrophilic plastomer is chosen from hydroxypropyl cellulose, hydroxypropylmethyl cellulose, polyethylene oxide, or a combination thereof.

5. The pharmaceutical composition of claim 1, wherein the hydrophilic elastomer is present in an amount from about 0.5% to about 40% by weight of the pharmaceutical composition.

6. The pharmaceutical composition of claim 1, wherein the deliquescent plasticizer is present in an amount from about 2% to about 50% by weight of the pharmaceutical composition.

7. The pharmaceutical composition of claim 1, wherein the solid dosage form further comprises a film coating.

8. The pharmaceutical composition of claim 1, wherein the at least one hydrophilic plastomer comprises hydroxypropyl cellulose, hydroxypropylmethyl cellulose, and polyethylene oxide and is present in an amount from about 50% to about 80% by weight of the composition; the hydrophilic elastomer is a carbomer and is present in an amount from 0.5% to about 10% by weight of the composition; and the deliquescent plasticizer comprises citric acid and sorbitol and is present in an amount from about 10% to about 30% by weight of the composition.

9. The pharmaceutical composition of claim 8, wherein the API is oxycodone, oxymorphone, hydrocodone, hydromorphone, codeine, or morphine.

10. The pharmaceutical composition of claim 1, which deters abuse by forming a viscous mixture or gel when contacted with 10 mL or less of an aqueous solvent.

11. The pharmaceutical composition of claim 1, wherein the relative humidity at step (b) is from about 40% to about 100% at 25° C.

12. The pharmaceutical composition of claim 1, wherein the heating step (e) occurs at a temperature from about 50° C. to about 90° C.

13. The pharmaceutical composition of claim 1, which deters abuse by breaking into a plurality of particles having an average diameter of greater than about 250 microns when crushed, ground, or pulverized.

* * * * *